United States Patent [19]

Barnett et al.

[11] Patent Number: 4,676,989

[45] Date of Patent: Jun. 30, 1987

[54] SWEETENING WITH CYCLOALKYL ETHERS AND THIOETHERS OF DIPEPTIDES

[75] Inventors: Ronald E. Barnett, Suffern; Paul R. Zanno, Nanuet; Glenn M. Roy, Garnerville, all of N.Y.

[73] Assignee: General Foods Corporation, White Plains, N.Y.

[21] Appl. No.: 885,106

[22] Filed: Jul. 14, 1986

Related U.S. Application Data

[62] Division of Ser. No. 686,577, Dec. 27, 1984, Pat. No. 4,638,071.

[51] Int. Cl.$^4$ .............................................. A23L 1/236
[52] U.S. Cl. .................................................... 426/548
[58] Field of Search ......................................... 426/548

[56] References Cited

U.S. PATENT DOCUMENTS 4,448,716 5/1984 Tsau ............................... 426/548 X Primary Examiner—Joseph M. Golian
Attorney, Agent, or Firm—Linn I. Grim; Thomas A. Marcoux; Daniel J. Donovan

[57] ABSTRACT

The following dipeptides possess a high order of sweetness:

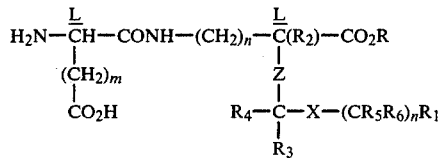

wherein
X=O or S;
R is alkyl containing 1-3 carbon atoms;
$R_1$ is cycloalkyl, cycloalkenyl, lower alkyl-substituted cycloalkyl or cycloalkenyl, bicycloalkyl, bicycloalkenyl, tricycloalkyl, cyclic ether, cyclic thioether, cyclic sulfoxides, cyclic sulfones, aryl, benzyl, alkylaryl, aromatic heterocyclic or alkyl substituted aromatic heterocyclic containing up to 10 ring carbon atoms and up to a total of 12 carbon atoms;
$R_2$, $R_3$, $R_4$ and $R_6$ are each H or lower alkyl;
$R_5$ is H, lower alkyl or cycloalkyl containing 3-5 ring carbons;
each n=0, 1 or 2;
m=0 or 1;
Z is an alkylene chain containing 0-2 carbon atoms in the principal chain and up to a total of 6 carbon atoms;
and food-acceptable salts.

25 Claims, No Drawings

SWEETENING WITH CYCLOALKYL ETHERS AND THIOETHERS OF DIPEPTIDES

This is a division of application Ser. No. 686,577, filed 12/2784 and now U.S. Pat. No. 4,638,071.

BACKGROUND OF THE INVENTION

1. Field of the Invention

This invention relates to a novel group of compounds and more particular to a novel group of compounds particularly well suited as sweeteners in edible foodstuff.

2. Description of the Prior Art

Sweetness is one of the primary taste cravings of both animals and humans. Thus, the utilization of sweetening agents in foods in order to satisfy this sensory desire is well established.

Naturally occurring carbohydrate sweeteners such as sucrose, are still the most widely used sweetening agents. While these naturally occurring carbohydrates, i.e., sugars, generally fulfill the requirements of sweet taste, the abundant usage thereof does not occur without deleterious consequence, e.g., high caloric intake and nutritional imbalance. In fact, oftentimes the level of these sweeteners required in foodstuffs is far greater than the level of the sweetener that is desired for economic, dietetic or other functional consideration.

In an attempt to eliminate the disadvantages concomitant with natural sweeteners, considerable research and expense have been devoted to the production of artificial sweeteners, such as for example, saccharin, cyclamate, dihydrochalcone, aspartame, etc. While some of these artificial sweeteners satisfy the requirements of sweet taste without caloric input, and have met with considerable commercial success, they are not, however, without their own inherent disadvantages. For example, many of these artificial sweeteners have the disadvantages of high cost, as well as delay in the perception of the sweet taste, persistent lingering of the sweet taste, and a very objectionable bitter, metallic aftertaste when used in food products.

Since it is believed that many disadvantages of aritificial sweeteners, particularly aftertaste, is a function of the concentration of the sweetener, it has been previously suggested that these effects could be reduced or eliminated by combining artificial sweeteners such as saccharin, with other ingredients such as aspartame or natural sugars, such as sorbitol, dextrose, maltose etc. These combined products, however, have not been entirely satisfactory either. Some U.S. Patents which disclose sweetener mixtures include for example, U.S. Pat. No. 4,228,198; U.S. Pat. No. 4,158,068; U.S. Pat. No. 4,154,862; and U.S. Pat. No. 3,717,477.

Accordingly, much work has continued in an attempt to develop and identify compounds that have a sweet taste and which will satisfy the need for better lower calorie sweeteners. Search continues for sweeteners that have intense sweetness, that is, deliver a sweet taste at low use levels and which will also produce enough sweetness at low levels to act as sole sweetener in all or most sweetener applications. Furthermore, the sweeteners sought must have good temporal and sensory qualities. Sweeteners with good temporal qualities produce a time-intensity sweetness responses similar to natural sweeteners without lingering. Sweeteners with good sensory qualities lack undesirable off tastes and aftertaste. Furthermore, these compounds must be economical and safe to use.

In U.S. Pat. No. 3,798,204 L-aspartyl-O-t-butyl-L-serine methyl ester and L-aspartyl-O-t-amyl-L-serine methyl ester are described as sweet compounds. These compounds, however, are not entirely satisfactory in producing a sweet response at low levels of sweetener.

In U.S. Pat. No. 4,448,716 metal complex salts of dipeptide sweeteners are disclosed. In the background of this patent a generic formula is described as an attempt to represent dipeptide sweeteners disclosed in five prior patents: U.S. Pat. No. 3,475,403; U.S. Pat. No. 3,492,131; Republic of South Africa Patent No. 695,083 published July 10, 1969; Republic of South Africa Patent No. 695,910 published Aug. 14, 1969; and German Patent No. 2,054,554. The general formula attempting to represent these patents is as follows:

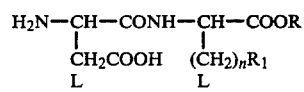

Wherein R represents the lower alkyls, lower alkyaryls and cycloalkyls, n stands for integers 0 through 5, $R_1$ represents (a) phenyl group, (b) lower alkyls, (c) cyclo-alkyls, (d) $R_2$.

Where $R_2$ is hydroxy, lower alkoxy, lower alkyl, halogen, (e) $(S(O))_m$ (lower alkyl) where m is 0, 1 or 2 and provided n is 1 or 2, (f) $R_3$.

Where $R_3$ represents an hydroxy or alkoxy and (g) single or double unsaturated cycloalkyls with up to eight carbons. These compounds also are not entirely satisfacory in producing a high quality sweetness or in producing a sweet response at low levels of sweetener.

Dipeptides of aspartyl-cysteine and aspartylmethionine methyl esters are disclosed by Brussel, Peer and Van der Heijden in *Chemical Senses and Flavour*, 4, 141–152 (1979) and in *Z. Lebensm. Untersuch-Forsch.*, 159, 337–343 (1975). The authors disclose the following dipeptides:

α-L-Asp-L-Cys(Me)-OMe
α-L-Asp-L-Cys(Et)-OMe
α-L-Asp-L-Cys(Pr)-OMe
α-L-Asp-L-Cys(i-Pr)-OMe
α-L-Asp-L-Cyst(t-But)-OMe
α-L-Asp-L-Met-OMe European Patent Application No. 34,876 described amides of L-aspartyl-D-amino acid dipeptides of the formula:

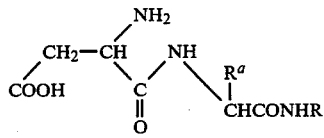

wherein $R^a$ is methyl, ethyl, n-propyl or isopropyl and R is a branched aliphatic, alicyclic or heterocyclic member which is branched at the alpha carbon atom and also branched again at one or both of the beta carbon atoms. These compounds are indicated to be of significant sweetness.

Despite the past efforts in this area, research continues. Accordingly, it is desired to find compounds that provide quality sweetness when added to foodstuffs or pharmaceuticals at low levels and thus eliminate or greatly diminish disadvantages associated with prior art sweeteners.

SUMMARY OF THE INVENTION

The present new compounds ar dipeptides of certain α-aminodicarboxylic acids and etherified hydroxy α-amino-mono-carboxylic acid esters which are low calorie sweeteners that possess a high order of sweetness, with pleasing taste and little, if any, aftertaste.

This invention provides new sweetening compounds represented by the formula:

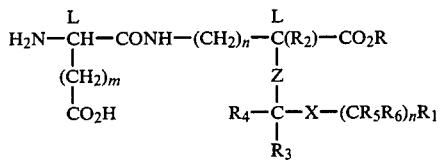

wherein
X=O or S;
R is alkyl containing 1-3 carbon atoms;
$R_1$ is cycloalkyl, cycloalkenyl, lower alkylsubstituted cycloalkyl or cycloalkenyl, bicycloalkyl, bicycloalkenyl, tricycloalkyl, cyclic ether, cyclic thioether, cyclic sulfoxides, cyclic sulfones, aryl, benzyl, alkylaryl, aromatic heterocyclic or alkyl substituted aromatic heterocyclic containing up to 10 ring carbon atoms and up to a total of 12 carbon atoms;
$R_2$, $R_3$, $R_4$ and $R_6$ are each H or lower alkyl;
$R_5$ is H, lower alkyl or cycloalkyl containing 3-5 ring carbons;
each n=0, 1 or 2;
m=0 or 1;
Z is an alkylene chain containing 0-2 carbon atoms in the principal chain and up to a total of 6 carbon atoms;
and food-acceptable salts.

Compounds of the above formula have a surprisingly high order of sweetness and pleasant taste and are particularly suitable for lower calorie sweetening of foods and pharmaceuticals.

DESCRIPTION OF THE PREFERRED EMBODIMENTS

In accordance with the present invention, the preferred novel compounds of the invention are represented by the formula:

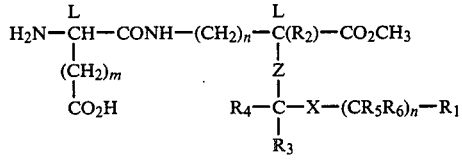

wherein m=0 or 1, and each n, Z and $R_1$-$R_6$ has the same meaning as in formula I.

Additional stereoisomers in the present new compound exist in those compounds wherein $R_4$ is not identical to $R_3$. Mixtures of these isomers are, of course, useful as sweeteners and are desired. The mixtures may be resolved into the corresponding D and L forms.

Especially preferred compounds of the formula

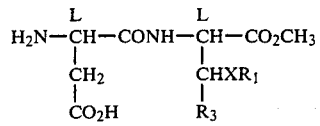

wherein $R_1$ and $R_3$ are as previously defined. These compounds are readily preparable and show the highest levels of sweetness.

The alpha aminodicarboxylic acids of the present new dipeptides are aspartic acid and aminomalonic acid, of which aspartic acid is preferred. The etherified mercapto and hydroxy alpha-aminomonocarboxylic acids are etherified serine, threonine and cysteine, and homologs thereof such as beta-hydroxy alpha-aminovaleric acid, gamma-hydroxy alpha-aminobutyric acid, gamma-hydroxy alpha-aminovaleric acid, beta-hydroxy alpha-aminobutyric acid, beta-mercapto alpha-aminovaleric acid, gamma-mercapto alpha-aminobutyric acid and similar such amino acids and lower alkyl esters. The ether group in these acids is a cyclic hydrocarbyl group comprising cycloalkyl, cycloalkenyl, bicycloalkyl, tricycloalkyl, bicycloalkenyl, cyclic ether, cyclic thioether, cyclic sulfoxides, cyclic sulfones, aryl, aralkyl, or a cyclic ether or thioether. The ether group is directly attached to the ether oxygen or sulfur, or separated by an alkylene chain from the ether oxygen or sulfur.

In accordance with the present sweetener taste testing, the preferred compounds are those in which the aminodicarboxylic acid group is α-aspartyl and the aminomonocarboxylic acid ester is cysteine, threonine or serine methyl ester, and of these, serine and cysteine methyl esters are preferred.

The ether groups of the present new compounds includes such groups as cycloalkyl, e.g., cyclobutyl, cyclopentyl, cyclohexyl, cycloheptyl, etc.; alkyl-substituted cycloalkyls, e.g., 1-methylcyclopentyl, 1-methylcyclohexyl, 1-methylcyclobutyl, 1-methylcycloheptyl, 1-ethylcyclobutyl, 1-ethylcyclopentyl, 1-ethylcycloheptyl, 1-ethylcyclohexyl, 1-isopropylcyclobutyl, 1-isopropylcyclopentyl, 1-isopropylcyclohexyl, 1-isopropylcycloheptyl, 1,2-dimethylcyclohexyl, 1,2-dimethylcyclopentyl, 1,2-dimethylcycloheptyl, 1,3-dimethylcyclohexyl, 1,3-dimethylcyclopentyl, 1,3-dimethylcycloheptyl, 1,4-dimethylcyclohexyl, 1,4-dimethylcycloheptyl, 2,3-dimethylcyclopentyl, 2,3-dimethylcyclohexyl, 2,3-dimethylcyclo-heptyl, 2,4-dimethylcyclopentyl, 2,4-dimethylcyclohexyl, 2,4-dimethylcycloheptyl, 2,5-dimethylcyclopenttyl, 2,5-dimethylcyclohexyl, 2,5-dimethylcycloheptyl, 2,6-dimethylcyclohexyl, 2,6-dimethylcycloheptyl, 2,7-dimethylcycloheptyl, 3,4-dimethylcyclopentyl, 3,4-dimethylcyclohexyl, 3,4-dimethylcycloheptyl, 3,5-dimethylcyclohexyl, 3,5-dimethylcycloheptyl, 4,5-dimethylcycloheptyl, 3,6-dimethylcyclohexyl, 3,6-dimethylcycloheptyl, 4,6-dimethylcycloheptyl, 5,6-dimethylcyclohexyl, 2,2-dimethylcyclopentyl, 2,2-dimethylcyclohexyl, 2,2-dimethylcycloheptyl, 3,3-dimethylcyclopentyl, 3,3-dimethylcyclohexyl, 3,3-dimethylcycloheptyl, 4,4-dimethylcyclohexyl, 4,4-dimethylcycloheptyl, 2,2,3-trimethylcyclopentyl, 2,2,3-trimethylcyclohexyl, 2,2,3-trimethylcycloheptyl, 2,2,4-trimethylcyclopentyl, 2,2,4-trimethylcyclohexyl, 2,2,4-trimethylcycloheptyl, 2,2,5-trimethylcyclopentyl, 2,2,5-trimethylcyclohexyl, 2,2,5-trimethylcycloheptyl, 2,2,6-trimethylcyclohexyl, 2,2,6-trimethylcyclohepty, 2,2,7-trimethylcycloheptyl, 1,2,2-trimethylcyclopentyl, 1,2,2- trimethylcyclohexyl, 1,2,2-trimethylcycloheptyl, 1,3,3-trimethylcyclopentyl, 1,3,3-trimethylcyclohexyl, 1,3,3-trimethylcycloheptyl, 1,4,4-trimethylcyclohexyl, 1,4,4-trimethylcyclopentyl, 3,3,4-trimethylcyclopentyl, 3,3,4-trimethylcyclohexyl, 3,3,4-trimethylcycloheptyl, 2,3,3-trimethylcyclopentyl, 2,3,3-trimethylcyclohexyl, 2,3,3-trimethylcycloheptyl, 2,4,4-trimethylcyclopentyl, 2,4,4-trimethylcyclohexyl, 2,4,4-trimethylcycloheptyl, 1,2,3-trimethylcyclopentyl, 1,2,3-trimethylcyclohexyl, 1,2,3-trimethylcycloheptyl, 1,2,4-trimethylcyclopentyl, 1,2,4-trimethylcyclohexyl, 1,2,4-trimethylcyclopheptyl, 1,2,5-trimethylcyclopentyl, 1,2,5-trimethylcyclohexyl, 1,2,5-trimethylcycloheptyl, 1,2,6-trimethylcyclohexyl, 1,2,6-trimethylcycloheptyl, 1,2,7-trimethylcycloheptyl, 2,3,4-trimethylcyclopentyl, 2,3,4-trimethylcyclohexyl, 2,3,4-trimethylcycloheptyl, 2,3,5trimethylcyclopentyl, 2,3,5-trimethylcyclohexyl, 2,3,5-trimethylcycloheptyl, 2,3,6-trimethylcyclohexyl, 2,3,6-trimethylcycloheptyl, 2,3,7-trimethylcycloheptyl, 3,4,4-trimethylcyclohexyl, 3,4,4-trimethyl, 2,2,5,5-tetramethylcyclopentyl, 2,2,5,5-tetramethylcyclohexyl, 2,2,5,5-tetramethylcycloheptyl, 2,2,6,6-tetramethylcyclohexyl, 2,2,6,6-tetramethylcycloheptyl, 2,2,7,7-tetramethylcycloheptyl, 2,2,4,4-tetramethylcyclopentyl, 2,2,4,4-tetramethylcyclohexyl, 2,2,4,4-tetramethylcycloheptyl, 2,2,3,3-tetramethylcyclopentyl, 2,2,3,3-tetramethylcyclohexyl, 2,2,3,3-tetramethylcycloheptyl, 3,3,4,4-tetramethylcyclopentyl, 3,3,4,4-tetramethylcyclohexyl, 3,3,4,4-tetramethylcycloheptyl, 3,3,5,5-tetramethylcyclohexyl, 3,3,5,5-tetramethylcycloheptyl, 1,2,3,4-tetramethylcyclopentyl, 1,2,3,4-tetramethylcyclohexyl, 1,2,3,4-tetramethylcycloheptyl, 1,2,3,5-tetramethylcyclopentyl, 1,2,3,5-tetramethylcyclohexyl, 1,2,3,5-tetramethylcycloheptyl, 1,2,3,6-tetramethylcyclohexyl, 1,2,3,6-tetramethylcycloheptyl, 2,3,4,5-tetramethylcyclopentyl, 2,3,4,5-tetramethylcyclohexyl, 2,3,4,5-tetramethylcycloheptyl, 2,3,4,6-tetrametthylcycloheptyl, 2,3,4,6-tetramethylcyclohexyl, 2,3,4,7-tetramethylcycloheptyl, 2,2,3,4-tetramethylcyclopentyl, 2,2,3,4-tetramethylcyclohexyl, 2,2,3,4-tetramethylcycloheptyl, 2,2,3,5-tetramethylcyclopentyl, 2,2,3,5-tetramethylcyclohexyl, 2,2,3,5-tetramethylcycloheptyl, 2,2,3,6-tetramethylcyclohexyl, 2,2,3,6-tetramethylcycloheptyl, 2,2,3,7-tetramethylcycloheptyl, 2,3,3,4-tetramethylcyclohexyl, 2,3,3,4-tetramethylcyclopentyl, 2,3,3,4-tetramethylcycloheptyl, 2,3,3,5-tetramethylcyclopentyl, 2,2,3,5-tetramethylcyclohexyl, 2,3,3,5-tetramethylcycloheptyl, 2,3,3,6-tetramethylcyclohexyl, 2,3,3,6-tetramethylcycloheptyl, 2,3,3,7-tetramethylcycloheptyl, 2,2,3,4-tetramethylcyclopentyl, 2,2,3,4-tetramethylcyclohexyl, 2,3,3,4-tetramethylcycloheptyl, 2,2,3,5-tetramethylcyclopentyl, 2,2,3,5-tetramethylcyclohexyl, 2,2,3,6-tetramethylcyclohexyl, 2,2,3,6-tetramethylcycloheptyl, 2,2,3,7-tetramethylcycloheptyl, 2,2,4,5-tetramethylcyclopentyl, 2,2,4,5-tetramethylcyclohexyl, 2,2,4,5-tetramethylcycloheptyl, 2,2,4,6-tetramethylcyclohexyl, 2,2,4,6-tetramethylcycloheptyl, 2,2,4,7-tetramethylcycloheptyl, 4-methylcyclohexylisopropyl, 4-methylcycloheptylisopropyl, 3-methylcyclopentylisopropyl, 3-methylcyclohexylisopropyl, 3-methylcycloheptylisopropyl, 2-methylcycloheptylisopropyl, 2-methylcyclohexylisopropyl, 2-methylcyclopentylisopropyl, dicyclopropylmethyl, t-butylcyclopropylmethyl, t-butylcyclopentylmethyl, 2-isopropylcyclopentyl, 2-t-butylcyclopentyl, 2-isopropylcyclohexyl, 2-t-butylcyclopentyl, 2-isopropylcyclohexyl, 2-t-butylcyclohexyl, 2-t-amylcyclopentyl, t-amylcyclopropylmethyl, dicyclobutylmethyl, t-butylcyclobutylmethyl, etc., cycloalkenes, e.g., cyclopentenyl, cyclohexenyl, cycloheptenyl, etc.; alkyl-substituted cycloalkenes, e.g., 1-methyl-3-cyclopentenyl, 1-methyl-3-cyclohexenyl, 1-methyl-3-cycloheptenyl, 1-methyl-4-cycloheptenyl, 3-cyclopentenylisopropyl, 3-cyclohexenylisopropyl, 3-cycloheptenylisopropyl, 4-cycloheptenylisopropyl, 3-cyclopentenylmethyl, 3-cyclopentenylethyl, 3-cyclohexenylpropyl, 3cyclohexenylethyl, 3-cycloheptenylpropyl, 3-cycloheptenylethyl, 4-cycloheptenylmethyl, 4-cycloheptenylethyl, 2-methyl-3-cyclohexenyl, 2-methyl-3-cyclopentenyl, 2-methyl-3-cycloheptenyl, 2-methyl-4-cycloheptenyl, 3-methyl-3-cyclohexenyl, 3-methyl-3-cyclopentenyl, 3-methyl-3-cycloheptenyl, 4-methyl-3-cycloheptenyl, 4-methyl-3-cyclohexenyl, 4-methyl-3-cyclopentenyl, 5-methyl-3-cyclopentenyl, 5-methyl-3-cyclohexenyl, 5-methyl-3-cycloheptenyl, 6-methyl-3-cyclohexenyl, 6-methyl-3-cycloheptenyl, 2-methyl-2-cyclopentenyl, 2-methyl-2-cyclohexenyl, 2-methyl-2-cycloheptenyl, 2-methyl-2-cyclopentenyl, 3-methyl-2-cyclohexenyl, 3-methyl-2-cycloheptenyl, 1-methyl-2-cyclopentenyl, 1-methyl-2-cyclohexenyl, 1-methyl-2-cycloheptenyl, 5-methyl-2-cyclopentenyl, 4-methyl-2-cyclohexenyl, 4-methyl-2-cycloheptenyl, 5-methyl-2-cyclohexenyl, 5-methyl-2-cycloheptenyl, 6-methyl-2-cyclohexenyl, 6-methyl-2-cycloheptenyl, 7-methyl-2-cycloheptenyl, 2,3-dimethyl-2-cyclopentenyl, 2,3-dimethyl-2-cyclohexenyl, 2,4-dimethyl-2-cyclopentenyl, 2,4-dimethyl-2-cyclohexenyl, 2,5-dimethyl-2-cyclohexenyl, 2,5-dimethyl-2-cycloheptenyl, 2,6-dimethyl-2-cyclohexenyl, 2,6-dimethyl-3-cyclohexenyl, 2,5-dimethyl-3-cyclohexenyl, 2,5-dimethyl-2-cyclopentenyl, 2,4-dimethyl-3-cyclopentenyl, 2,4-dimethyl-3-cyclohexenyl, 3,3-dimethyl-3-cyclopentenyl, 3,3-dimethyl-3-cyclohexenyl, 3,4-dimethyl-3-cyclopentenyl, 3,4-dimethyl-3-cyclohexenyl, 4,5-dimethylcyclo-3-pentenyl, 4,5-dimethyl-3-cyclo-3-hexenyl, 5,5-dimethyl-3-cyclohexenyl, 5,5-dimethylcyclopentenyl, 5,5-dimethylcyclohexenyl, 6,6-dimethylcyclohexenyl, 1,2-dimethyl-3-cyclopentenyl, 1,2-dimethyl-3-cyclohexenyl, 1,3-dimethyl-3-cyclopentenyl, 1,3-dimethyl-3-cyclohexenyl, 1,3-dimethyl-3-cycloheptenyl, 1,4-dimethyl-3-cyclopentenyl, 1,4-dimethyl-3-cyclohexenyl, 1,4-dimethyl-3-cyclohexenyl, 1,5-dimethyl-3-cyclopentenyl, 1,5-dimethyl-3-cyclohexenyl, 1,5-dimethyl-3-cycloheptenyl, 2,2,6-trimethyl-3-cyclohexenyl, 2,2,5-trimethyl-3-cyclohexenyl, 2,5,5-trimethyl-3-cyclohexenyl, 2,5,5-trimethyl-3-cyclopentenyl, 2,7,7-trimethyl-3-cycloheptenyl, 2,7,7-trimethyl-4-cycloheptenyl, 2,2,7-trimethyl-3-cycloheptenyl, 2,2,7-trimethyl-4-cycloheptenyl, 2,3,6-trimethyl-3-cyclohexenyl, 2,3,7-trimethyl-3-cycloheptenyl, 2,3,5-trimethyl-3-cyclopentenyl, 2,2,6,6-tetramethyl-3-cyclohexenyl, 2,2,5,5-tetramethyl-3-cyclopentenyl, 2,2,7,7-tetramethyl-3-cycloheptenyl, 2,3,5,5-tetramethyl-3-cyclopentenyl, 2,3,6,6-tetramethyl-3-cyclohexenyl, 2,3,7,7-tetramethyl-3-cycloheptenyl, 2,3,6,6-tetramethyl-3-cycloheptenyl, 2,3,5,5-tetramethyl-3-cyclohexenyl, 2,3,4,5-tetramethyl-3-cyclopentenyl, 2,3,4,5-tetramethyl-3-cyclohexenyl, (4-ethylcyclohex-3-enyl)isopropyl, (4-propylcyclohex-3-enyl)isopropyl, (4-methylcyclohex-3-enyl)ethyl, (3-methylcyclohex-3-enyl)isopropyl, (4-ethylcyclopent-3-enyl)isopropyl, (4-propylcyclopent-3-enyl)isopropyl, (4-methylcyclopent-3-enyl)isopropyl, (4-methylcyclopent-3-enyl)ethyl, (3-methylcyclopent-3-enyl)isopropyl, (2-methylcyclohex-3-enyl)isopropyl, (2-methylcyclopent-3-enyl)isopropyl, etc.; bicyclic compounds, such as norbornyl, norcaranyl, norpinanyl, bicyclo[2.2.2]octyl, etc.; alkyl substituted bicyclic compounds, e.g., 6,6-dimethyl bicyclo[3.1.1]heptyl, 6,7,7-trimethylnorbornyl(bornyl), pinanyl, thujanyl, caranyl, fenchyl, 2-norbornylmethyl, 2-norbornylethyl, 2-norbornylpropyl, 3-norbornylpropyl, etc.; unsubstituted and alkyl-substituted bicycloalkenes such as norborenyl, norpinenyl, norcarenyl, 2-(4-norborenyl)ethyl, pinenyl, carenyl, fenchenyl, etc., tricyclocompounds such as adamantyl and alkyl-substituted adamantyl, etc., and cyclic ethers, such as 2,3-dihydrofuryl, 2,3-dihydropyranyl, 3,4-dihydropyranyl, tetrahydrofuryl, tetrahydropyranyl; alkyl substituted cyclic ethers, such as 3-(2,2-dimethyltetrahydrofuryl), 3-(4,4-dimethyltetrahydrofuryl), 3-(2,3-dimethyltetrahydrofuryl), 3-(2,4-dimethyltetrahydrofuryl), 3-(2,5-dimethyltetrahydrofuryl), 3-(3,4-dimethyltetrahydrofuryl), 3-(3,5-dimethyltetrahydrofuryl), 3-(4,5-dimethyltetrahydrofuryl), 2-(3,3-dimethyltetrahydrofuryl), 2-(4,4-dimethyltetrahydrofuryl), 2-(5,5-dimethyltetrahydrofuryl), 2-(2,3-dimethyletetrahydrofuryl), 2-(2,4-dimethyltetrahydrofuryl), 2-(2,5-dimethyltetrahydrofuryl), 2-(3,4-dimethyltetrahydrofuryl), 2-(3,5-dimethyltetrahydrofuryl), 2-(4,5-dimethyltetrahydrofuryl), 3-(4,5-dimethyltetrahydrofuryl), 3-(2,2,3-trimethyltetrahydrofuryl), 3-(2,2,4-trimethyltetrahydrofuryl), 3-(2,2,5-trimethyltetrahydrofuryl), 3-(2,3,4-trimethyltetrahydrofuryl, 3-(2,3,5-trimethyltettahydrofuryl), 3-(2,4,5-trimethyltetrahydrofuryl), 3-(2,5,5-trimethyltetrahydrofuryl), 3-(3,4,4-trimethyltetrahydrofuryl, 3-(3,5,5-trimethyltetrahydrofuryl), 3-(4,5,5-trimethyltetrahydrofuryl), 3-(2,2,5,5-tetramethylhydrofuryl), 2-(2,2,4,4-tetramethylhydrofuryl), 3-(2,3,4,5-tetramethylhydrofuryl), 3-(2,4,5,5-tetramethylhydrofuryl), 3-(2,3,5,5-tetramethylhydrofuryl), 2-(2,3,3-trimethyltetrahydrofuryl), 2-(2,3,4-trimethyltetrahydrofuryl), 2-(2,3,5-trimethyltetrahydrofuryl), 2-(2,4,5-trimethyltetrahydrofuryl), 2-(2,5,5-trimethyltetrahydrofuryl), 2-(3,3,4-trimethyltetrahydrofuryl), 2-(3,3,5-trimethyltetrahydrofuryl), 2-(3,4,5-trimethyltetrahydrofuryl), 2-(4,4,5-trimethyltetrahydrofuryl), 2-(2,3,3,4-tetramethylhydrofuryl), 2-(2,3,3,5-tetramethylhydrofuryl), 2-(2,3,4,5-tetramethylhydrofuryl), 2-(2,3,5,5-tetramethylhydrofuryl), 2-(2,3,4,4-tetramethylhydrofuryl), 2-(2,3,5,5-tetramethylhydrofuryl), 2-(3,3,4,5-tetramethylhydrofuryl), 2-(3,3,5,5-tetramethylhydrofuryl), 2-(3,4,5,5-tetramethylhydrofuryl), 2-(2,3,4,5-tetramethylhydrofuryl), 2-(4,4,5,5-tetramethylhydrofuryl), 3-furylmethyl, 2-furylmethyl, 2-(5-methylfuryl)methyl, and the corresponding furfuryl compounds, and the corresponding tetrahydropyranyls, as well as the corresponding 2,3-dihydrofuryl, 2,3-dihydropyranyl, 3,4-dihydropyranyl, as well as the corresponding cyclic thioethers, such as 2-thienylmethyl, 3-thienylmethyl, 2-(5-methylthienyl)methyl, etc., and the corresponding cyclic sulfones or cyclic sulfoxides thereof; aryl or alkylaryl, such as phenyl, 2,6-dimethylphenyl, 2,5-dimethylphenyl, 2,4-dimethylphenyl, 2,3-dimethylphenyl, 3,4-dimethylphenyl, 3,5-dimethylphenyl, 3,6-dimethylphenyl, 2,3,4-trimethylphenyl, benzyl, α-methylbenzyl, o-methylbenzyl, etc.

The preferred $R_1$ is cycloalkyl or alkyl-substituted cycloalkyl, especially where the alkyl group is in the α, β, or β' positions. Further preferred groups include alkyl-substituted furyl, thienyl, dihydro- and tetrahydrofuryl, phenyl and o- and m-alkylphenyl. Further preference exists for compounds in which $R_1$ is a cycloalkyl with one, two, three, or four alkyl groups in the β, β' positions such as β, β, β', β'-tetraalkyl-substituted cyclopentyl, cyclohexyl, and cycloheptyl, as well as β,β,β'-trialkyl substituted and β,β,β'-trisubstituted-cyclohexyl, cyclopentyl, and cycloheptyl.

Illustrated preferred compounds include.

α-L-aspartyl-O-(1-methylcyclobutyl)-L-serine methyl ester

α-L-aspartyl-O-cyclopentyl-L-serine methyl ester

α-L-aspartyl-O-(1-methylcyclopentyl)-L-serine methyl ester

α-L-aspartyl-O-(1-ethylcyclopentyl)-L-serine methyl ester

α-L-aspartyl-O-(1-propylcyclopentyl)-L-serine methyl ester

α-L-aspartyl-O-(1-isopropylcyclopentyl)-L-serine methyl ester

α-L-aspartyl-O-(1,2-dimethylcyclopentyl)-L-serine methyl ester

α-L-aspartyl-O-(1,2,5-trimethylcyclopentyl)-L-serine methyl ester

α-L-aspartyl-O-(1,2,2-trimethylcyclopentyl)-L-serine methyl ester

α-L-aspartyl-O-(2,2,5,5-tetramethylcyclopentyl)-L-serine methyl ester

α-L-aspartyl-O-cyclohexyl-L-serine methyl ester

α-L-aspartyl-O-(1-methylcyclohexyl)-L-serine methyl ester

α-L-aspartyl-O-(1-ethylcyclohexyl)-L-serine methyl ester

α-L-aspartyl-O-(1-propylcyclohexyl)-L-serine methyl ester

α-L-aspartyl-O-(1-isopropylcyclohexyl)-L-serine methyl ester

α-L-aspartyl-O-(1,2-dimethylcyclohexyl)-L-serine methyl ester

α-L-aspartyl-O-(1,2,6-trimethylcyclohexyl)-L-serine methyl ester

α-L-aspartyl-O-(1,2,2-trimethylcyclohexyl)-L-serine methyl ester

α-L-aspartyl-O-(2,2,6,6-tetramethylcyclohexyl)-L-serine methyl ester

α-L-aspartyl-O-cycloheptyl-L-serine methyl ester

α-L-aspartyl-O-(1-methylcycloheptyl)-L-serine methyl ester

α-L-aspartyl-O-(1-ethylcycloheptyl)-L-serine methyl ester

α-L-aspartyl-O-(1-propylcycloheptyl)-L-serine methyl ester

α-L-aspartyl-O-(1-isopropylcycloheptyl)-L-serine methyl ester

α-L-aspartyl-O-(1,2-dimethylcycloheptyl)-L-serine methyl ester

α-L-aspartyl-O-(1,2,7-trimethylcycloheptyl)-L-serine methyl ester

α-L-aspartyl-O-(1,2,2-trimethylcyclohelptyl)-L-serine methyl ester

α-L-aspartyl-O-(2,2,7,7-tetramethylcycloheptyl)-L-serine methyl ester

α-L-aspartyl-[O-(3-methylcyclohexyl)]-L-serine methyl ester

α-L-aspartyl-[O-(3-methylcyclopentyl)]-L-serine methyl ester

α-L-aspartyl-[O-(1-methylcyclopentyl)]-L-threonine methyl ester

α-L-aspartyl-[O-2,2,5,5-tetramethylcyclopentyl]-L-serine methyl ester

α-L-aspartyl-O-(2,2,6,6-tetramethylcyclohexyl-L-serine methyl ester

α-L-aspartyl-O-(1,2,7-trimethylcycloheptyl)-L-serine methyl ester

α-L-aspartyl-O-(1,2,2-trimethylcycloheptyl)-L-serine methyl ester
α-L-aspartyl-O-(2,2,7,7-tetramethylcycloheptyl)-L-serine methyl ester
α-L-aspartyl-[O-(2,2,5-trimethylcyclopentyl)]-L-serine methyl ester
α-L-aspartyl-[O-(2,2-dimethylcyclopentyl)]-L-serine methyl ester
α-L-aspartyl-[O-(2,5-dimethylcyclopentyl)]-L-serine methyl ester
α-L-aspartyl-[O-(2,6-dimethylcyclohexyl)]-L-serine methyl ester
α-L-aspartyl-[O-2,2,6-trimethylcyclohexyl]-L-serine methyl ester
α-L-aspartyl-S-(1-methylcyclobutyl)-L-cysteine methyl ester
α-L-aspartyl-S-cyclopentyl-L-cysteine methyl ester
α-L-aspartyl-S-(1-methylcyclopentyl)-L-cysteine methyl ester
α-L-aspartyl-S-(1-ethylcyclopentyl)-L-cysteine methyl ester
α-L-aspartyl-S-(1-propylcyclopentyl)-L-cysteine methyl ester
α-L-aspartyl-S-(1-isopropylcyclopentyl)-L-cysteine methyl ester
α-L-aspartyl-S-(1,2-dimethylcyclopentyl)-L-cysteine methyl ester
α-L-aspartyl-S-(1,2,5-trimethylcyclopentyl)-L-cysteine methyl ester
α-L-aspartyl-S-(1,2,2-trimethylcyclopentyl)-L-cysteine methyl ester
α-L-aspartyl-S-(2,2,5,5-tetramethylcyclopentyl)-L-cysteine methyl ester
α-L-aspartyl-S-cyclohexyl-L-cysteine methyl ester
α-L-aspartyl-S-(1-methylcyclohexyl)-L-cysteine methyl ester
α-L-aspartyl-S-(1-ethylcyclohexyl)-L-cysteine methyl ester
α-L-aspartyl-S-(1-propylcyclohexyl)-L-cysteine methyl ester
α-L-aspartyl-S-(1-aspartyl-S-(1-isopropylcyclohexyl)-L-cysteine methyl ester
α-L-aspartyl-S-(1-isopropylcyclohexyl)-L-cysteine methyl ester
α-L-aspartyl-S-(1,2-dimethylcyclohexyl)-L-cysteine methyl ester
α-L-aspartyl-S-(1,2,6-trimethylcyclohexyl)-L-cysteine methyl ester
α-L-aspartyl-S-(1,2,2-trimethylcyclohexyl)-L-cysteine methyl ester
α-L-aspartyl-S-(2,2,6,6-tetramethylcyclohexyl)-L-cysteine methyl ester
α-L-aspartyl-S-cycloheptyl-L-cysteine methyl ester
α-L-aspartyl-[O-(2,2-dimethylcyclopentyl)]-L-serine methyl ester
α-L-aspartyl-[O-(2,2-dimethylcyclohexyl)]-L-serine methyl ester
α-L-aspartyl-[O-(2,2,4,4-tetramethylcyclobutyl)]-L-serine methyl ester
α-L-aspartyl-[O-(2-methylcyclopentyl)]-L-serine methyl ester
α-L-aspartyl-[O-(2-methylcyclohexyl)]-L-serine methyl ester
α-L-aspartyl-[O-(2-isopropylcyclopentyl)]-L-serine methyl ester
α-L-aspartyl-[O-(2-isopropylcyclohexyl)]-L-serine methyl ester
α-L-aspartyl-[O-(2-t-butylcyclopentyl)]-L-serine methyl ester
α-L-aspartyl-[O-(2-t-butylcyclohexyl)]-L-serine methyl ester
α-L-aspartyl-[O-(dicyclopropylmethyl)]-L-serine methyl ester
α-L-aspartyl-[O-(dicyclobutylmethyl)]-L-serine methyl ester
α-L-aspartyl-[O-(t-butylcyclopropylmethyl)]-L-serine methyl ester
α-L-aspartyl-[O-(t-butylcyclobutylmethyl)]-L-serine methyl ester
α-L-aspartyl-[O-(fenchyl)]-L-serine methyl ester
α-L-aspartyl-[O-(benzyl)]-L-serine methyl ester
α-L-aspartyl-[O-(α-methylbenzyl)]-L-serine methyl ester
α-L-aspartyl-[O-(o-methylbenzyl)]-L-serine methyl ester
α-L-aspartyl-[O-(2-furylmethyl)]-L-serine methyl ester
α-L-aspartyl-[O-(3-furylmethyl)]-L-serine methyl ester
α-L-aspartyl-[O-2-(5-methylfuryl)methyl]-L-serine methyl ester
α-L-aspartyl-[O-(2-thienylmethyl)]-L-serine methyl ester
α-L-aspartyl-[O-(3-thienylmethyl)]-L-serine methyl ester
α-L-aspartyl-[O-2-(5-methylthienyl)methyl]-L-serine methyl ester
α-L-aspartyl-S-(1-methylcycloheptyl)-L-cysteine methyl ester
α-L-aspartyl-S-(1-ethylcycloheptyl)-L-cysteine methyl ester
α-L-aspartyl-S-(1-propylcycloheptyl)-L-cysteine methyl ester
α-L-aspartyl-S-(1-isopropylcycloheptyl)-L-cysteine methyl ester
α-L-aspartyl-S-(1,2-dimethylcycloheptyl)-L-cysteine methyl ester
α-L-aspartyl-S-(1,2,7-trimethylcycloheptyl)-L-cysteine methyl ester
α-L-aspartyl-S-(1,2,2-trimethylcycloheptyl)-L-cysteine methyl ester
α-L-aspartyl-S-(2,2,7,7-tetramethylcycloheptyl)-L-cysteine methyl ester
α-L-aspartyl-[S-(3-methylcyclohexyl)]-L-cysteine methyl ester
α-L-aspartyl-[S-(3-methylcyclopentyl)]-L-cysteine methyl ester
α-L-aspartyl-[S-(2,2,5,5-tetramethylcyclopentyl)]-L-cysteine methyl ester
α-L-aspartyl-[S-(2,2,6,6-tetramethylcyclohexyl)]-L-cysteine methyl ester
α-L-aspartyl-[S-(1,2,7-trimethylcycloheptyl)]-L-cysteine methyl ester
α-L-aspartyl-[S-(1,2,2-trimethylcycloheptyl)]-L-cysteine methyl ester
α-L-aspartyl-[S-(2,2,7,7-tetramethylcycloheptyl)]-L-cysteine methyl ester
α-L-aspartyl-[S-(2,2,5-trimethylcyclopentyl)]-L-cysteine methyl ester
α-L-aspartyl-[S-(2,2-dimethylcyclopentyl)]-L-cysteine methyl ester
α-L-aspartyl-[S-(2,5-dimethylcyclopentyl)]-L-cysteine methyl ester
α-L-aspartyl-[S-(2,6-dimethylcyclohexyl)]-L-cysteine methyl ester
α-L-aspartyl-[S-(2,2,6-trimethylcyclohexyl)]-L-cysteine methyl ester α-L-aspartyl-[S-(2,2-dimethylcyclopentyl)]-L-cysteine methyl ester
α-L-aspartyl-[S-(2,2-dimethylcyclohexyl)]-L-cysteine methyl ester
α-L-aspartyl-[S-(2,2,4,4-tetramethylcyclobutyl)]-L-cysteine methyl ester
α-L-aspartyl-[S-(2-methylcyclopentyl)]-L-cysteine methyl ester
α-L-aspartyl-[S-(2-methylcyclohexyl)]-L-cysteine methyl ester
α-L-aspartyl-[S-(2-isopropylcyclopentyl)]-L-cysteine methyl ester
α-L-aspartyl-[S-(2-isopropylcyclohexyl)]-L-cysteine methyl ester
α-L-aspartyl-[S-(2-t-butylcyclopentyl)]-L-cysteine methyl ester
α-L-aspartyl-[S-(2-t-butylcyclohexyl)]-L-cysteine methyl ester
α-L-aspartyl-[S-(dicyclopropylmethyl)]-L-cysteine methyl ester
α-L-aspartyl-[S-(dicyclobutylmethyl)]-L-cysteine methyl ester
α-L-aspartyl-[S-(t-butylcyclopropylmethyl)]-L-cysteine methyl ester
α-L-aspartyl-[S-(t-butylcyclobutylmethyl)]-L-cysteine methyl ester
α-L-aspartyl-[S-(fenchyl)]-L-cysteine methyl ester
α-L-aspartyl-[S-(benzyl)-L-cysteine methyl ester
α-L-aspartyl-[S-(α-methylbenzyl)]-L-cysteine methyl ester
α-L-aspartyl-[S-(o-methylbenzyl)]-L-cysteine methyl ester
α-L-asparyl-[S-(2-furylmethyl)]-L-cysteine methyl ester
α-L-aspartyl-[S-(3-furylmethyl)]-L-cysteine methyl ester
α-L-aspartyl-[S-2-(5-methylfuryl)methyl]-L-cysteine methyl ester
α-L-aspartyl-[S-(2-thienylmethyl)]-L-cysteine methyl ester
α-L-aspartyl-[S-(3-thienylmethyl)]-L-cysteine methyl ester
α-L-aspartyl-[S-2-(5-methylthienyl)methyl]-L-cysteine methyl ester Furthermore, when the sweetness agents of the present invention are added to ingesta, the sweetness agents may be added alone or with nontoxic carriers such as the abovementioned sweeteners or other food ingredients such as acidulants and natural and artificial gums. Typical foodstuffs, and pharmaceutical preparations, in which the sweetness agents of the present invention may be used are, for example, beverages including soft drinks, carbonated beverages, ready to mix beverages and the like, infused foods (e.g. vegetables or fruits), sauces, condiments, salad dressings, juices, syrups, desserts, including puddings, gelatin and frozen desserts, like ice creams, sherbets, icings and flavored frozen desserts on sticks, confections, toothpaste, mouthwash, chewing gum, cereals, baked goods, intermediate moisture foods (e.g. dog food) and the like.

In order to achieve the effects of the present invention, the compounds described herein are generally added to the food product at a level which is effective to perceive sweetness in the food stuff and suitably is in an amount in the range of from about 0.0005 to 2% by weight based on the consumed product. Greater amounts are operable but not practical. Preferred amounts are in the range of from about 0.001 to about 1% of the foodstuff. Generally, the sweetening effect provided by the present compounds is experienced over a wide pH range, e.g. 2 to 10 preferably 3 to 7 and in buffered and unbuffered formulations.

It is desired that when the sweetness agents of this invention are employed alone or in combination with another sweetener, the sweetener or combination of sweeteners provide a sucrose equivalent in the range of from about 2 weight percent to about 40 weight percent and more preferably from about 3 weight percent of about 15 weight percent in the foodstuff or pharmaceutical.

A taste procedure for determination of sweetness merely involves the determination of sucrose equivalency. Sucrose equivalence for sweeteners are readily determined. The amount of a sweetener that is equivalent to a given weight percent sucrose can be determined by having a panel of tasters taste solutions of a sweetener at known concentrations and match its sweetness to standard solutions of sucrose.

In order to prepare compounds of the present invention several reaction schemes may be employed. In one reaction scheme compounds of the general formuals II (protected α-aminodicarboxylic acid) and III (protected etherified hydroxy or mercapto amino acid alkyl ester are condensed to form compounds of the general formula IV (protected L-aminodicarboxyl-O-cycloalkyl-l-hydroxyamino acid alkyl ester ethers or the protected L-aminodicarboxyl-S-cycloalkyl-L-mercaptoamino alkyl ester ethers). Susequent removal of protecting groups A and B from compounds of general formula Iv give the desired compounds of general formula I.

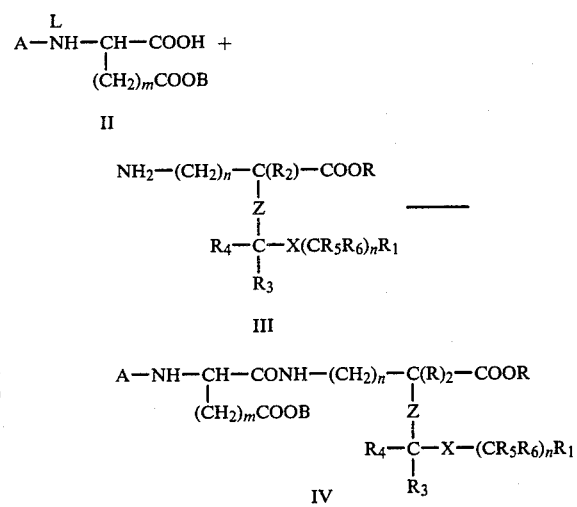

In these, group A is an amino protecting group, B is a carboxyl protecting group and R, $R_1$, $R_2$, $R_3$, $R_4$, $R_5$, $R_6$, Z, X, m and n have the same meaning as previously described. A variety of protecting groups known in the art may be employed. Examples of many of these possible groups may be found in "Protective Groups in Organic Synthesis" by T. W. Green, John Wiley and Sons, 1981. Among the preferred groups that may be employed are benzyloxycarbonyl for A and benzyl for B.

Coupling of compounds with general formula II to compounds having general formula III employs established techniques in peptide chemistry. One such technique uses dicyclohexylcarbodiimide (DCC) as the coupling agent. The DCC method may be employed with or without additives such as 4-dimethylaminopyridine or copper (II). The DCC coupling reaction generally proceeds at room temperature, however, it may be carried out from about −20° to 50° C. in a variety of solvents inert to the reactants. Thus suitable solvents include, but are not limited to, N,N-dimethyl-formamide, methylene chloride, toluene and the like. Preferably the reaction is carried out under an inert atmosphere such as argon or nitrogen. Coupling usually is complete within 2 hours but may take as long as 24 hours depending on reactants Various other methods can be employed to prepare the desired compounds. The following illustrates such methods using aspartic acid as the amino dicarboxylic acid and serine as the amino monocarboxylic acid. Of course, other amino di- and monocarboxylic acids can be substituted for these exemplary acids.

For example, U.S. Pat. Nos. 3,786,039; 3,833,553; 3,879,372 and 3,933,781 disclose the reaction of N-protected aspartic anhydrides with amino acids and amino acid derivatives to yield the desired products. These N-protected aspartic anhydrides can be reacted with compounds of formula III by methods disclosed in the above patents. As described in U.S. Pat. No. 3,786,039 compounds of formula III can be reacted directly in inert organic solvents with L-aspartic anhydride having its amino group protected by a formyl, carbobenzyloxy, or p-methoxycarbobenzyloxy group which is subsequently removed after coupling to give compounds of general formula I. The N-acyl-L-aspartic anhydrides are prepared by reacting the corresponding acids with acetic anhydride in amounts of 1.0–1.2 moles per mole of the N-acyl-L-aspartic acid at 0° to 60° C. in an inert solvent. The N-acyl-L-aspartic anhydrides are reacted with preferably 1 to 2 moles of compounds of formula III in an organic solvent capable of dissolving both the inert to the same. Suitable solvents are, but not limited to, ethyl acetate, methyl propionate, tetrahydrofuran, dioxane, ethyl ether, N,N-dimethylformamide and benzene. The reaction proceeds smoothly at 0° to 30° C. The N-acyl group is removed after coupling by catalytic hydrogenation with palladium on carbon or with HBr or HCl in a conventional manner. U.S. Pat. No. 3,879,372 discloses that this coupling method can also be performed in an aqueous solvent at a temperature of −10° to 50° C. and at a pH of 4–12.

Another method for the synthesis of the desired compounds is the reaction of compounds of formula III with suitable aspartic acid derivatives in which protecting groups have been attached to the amino and beta-carboxy groups and the alpha carboxy group has been converted to a reactive ester function. As disclosed in U.S. Pat. 3,475,403 these coupled products may be deprotected as described to yield the desired compounds of formula I.

An alternative scheme to the desired coupled compounds involves reaction of compounds of formula III with L-aspartic acid N-thiocarboxyanhydride by the method of Vinick and Jung, Tet. Lett., 23, 1315–18 (1982). An additional coupling method is described by T. Miyazawa, Tet. Lett., 25, 771 (1984).

Compounds of general formula III may be synthesized from N-protected serine methyl ester by employing a variety of etherification methods known in the art. Some of these methods may be found in "Modern Synthetic Reactions", 2nd ed., by H. O. House, W. A. Benjamin Inc., 1972; "Advanced Organic Chemistry," 2nd ed., by J. March, McGraw-Hill, 1977, and "Compendium of Organic Synthetic Methods," Vol. 1 and 2, by I. T. Harrison & S. Harrison, Wiley-Interscience, 1971 & 1974.

One possible etherification method is the acid catalyzed reaction of N-protected serine methyl ester with an appropriate olefinic precursor of the desired $R_1$ moiety. For example, when N-carbobenzyloxy-L-serine is reacted with methylene cyclopentane the N-protected intermediate of general formula III where $R_1$ represents 1-methyl cyclopentane is obtained. This intermediate is then deprotected to give a compound of formula III having $R_1$ equal to 1-methyl cyclopentane. When cycloalkadienes are used, the product is a cycloalkenyl ether. As illustrative examples, the following $R_1$ olefinic precursors can be utilized to give the corresponding saturated $R_1$ group:

| $R_1$ Precursor | $R_1$ Group |
|---|---|
| methylenecyclobutane | 1-methylcyclobutyl |
| 1-methyl-1-cyclobutene | 1-methylcyclobutyl |
| 1-methyl-1-cyclopentene | 1-methylcyclopentyl |
| 1-methyl-1-cyclohexene | 1-methylcyclohexyl |
| methylenecyclohexane | 1-methylcyclohexyl |
| 1,2-dimethyl-1-cyclohexene | 1,2-dimethylcyclohexyl |
| 1-methyl-1-cycloheptene | 1-methylcycloheptyl |
| 1-ethyl-1-cyclohexene | 1-ethylcyclohexyl |
| 1-ethyl-1-cyclopentene | 1-ethylcyclopentyl |
| 1,3-cyclopentadiene | 2-cyclopentenyl |
| 1-methyl-1,4-cyclohexadiene | 1-methyl-1-cyclohex-3-enyl |
| d-limonene | (1,1-dimethyl)-1-(4-methylcyclohex-3-enyl)-methyl |

The reaction of an appropriate olefinic $R_1$ precursor with N-protected serine methyl ester is preferably carried out in the presence of an acid catalyst. Any acid is employable but a mineral acid such as sulfuric acid is advantageous. Usually an excess of from 1.2 to 50 moles of the olefin precursor is utilized. Reaction temperatures are in the range of −10° to 40° C. and reaction times range from 2 to 48 hours. The reaction is carried out in a solvent that will dissolve both reactants and is inert to both as well. Solvents include, but are not limited to, methylene chloride, toluene, tetrahydrofuran, chloroform and the like. Usually an inert atmosphere of nitrogen or argon is supplied.

Another possible etherification method is the base, or other catalyst, promoted reaction of N-protected serine methyl ester with an $R_1X$, where X is an organic leaving group such as halide, tosylate or mesylate. Any base normally employed to deprotonate an alcohol may be used, such as sodium hydride, sodium hydroxide, triethylamine, or diisopropyl ethylamine. Reaction temperatures are in the range of −78° to 100° C. and reaction times vary from 2 to 48 hours. The reaction is carried out in a solvent that will dissolve both reactants and is inert to both as well. Solvents include, but are not limited to, diethyl ether, tetrahydrofuran, N,N-dimethylformamide, dimethylsulfoxide, and the like. Usually an inert atmosphere of nitrogen or argon is supplied.

Alternatively, a neutral catalyst such as mercury (II) salts or nickel (II) 2,4-pentanedionate may be employed in this reaction. These reactions are also carried out in inert solvents at room temperature or above. The intermediate formed in this reaction is deprotected to yield compounds of formula III.

A third method is the solvomercuration-demercuration reaction of the appropriate olefinic precursor of $R_1$ with N-protected serine methyl ester. The reaction of the olefin with N-protected serine methyl ester in the presence of mercuric acetate or mercury trifluoroacetate is carried out at a reaction temperature of −10° to 100° C. in a solvent which will dissolve both reactants and is inert to both. Solvents include, but are not limited to, diethyl ether, tetrahydrofuran, methylene chloride, and the like. Reaction times vary from 5 minutes to 24 hours. The resulting organomercury intermediate is reduced in situ with basic aqueous sodium borohydride, or other reducing agents, to remove the mercury, followed by deprotection to yield compounds of general formula III.

A fourth method of etherification is the reaction of N-protected beta-X-L-alanine methyl ester, where X is halide, tosylate, mesylate or other leaving group, with $R_1OH$ using a base or other catalyst. Any base normally employed to deprotonate an alcohol may be used, including sodium hydride, sodium hydroxide, triethylamine, or diisopropyl ethylamine. The reaction may be run either with or without additives, for example, copper salts. Reaction temperatures are in the range of −78° C. to 100° C., and reaction times vary from 2 to 48 hours. The reaction is carried out in a solvent that will dissolve both reactants and is inert to both. Solvents include, but are not limited to, diethyl ether, tetrahydrofuran, N,N-dimethylformamide, dimethylsulfoxide, and the like. Usually an inert atmosphere of nitrogen or argon is supplied.

Alternatively, a neutral catalyst such as mercury (II) salts or nickel (II) 2,4-pentanedionate may be employed in this reaction. These are also carried out in inert solvents at room temperature or above. This product is then deprotected to yield compounds of general formula III.

To prepare compounds in which $R_2$ and $R_3$ are alkyl, the starting compound should have a corresponding side chain with a double bond within the corresponding side chain, as exemplified by limonene, in which the side chain is

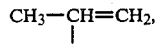

in which case 1,2 addition occurs on the side chain and does not involve ring carbon atoms.

With regard to the removal of protecting groups from compounds of formula IV and N-protected precursors of formula III, a number of deprotecting techniques are known in the art and can be utilized to advantage depending on the nature of the protecting groups. Among such techniques is catalytic hydrogenation utilizing palladium on carbon or transfer hydrogenation with 1,4-cyclohexadiene. Generally the reaction is carried at room temperature but may be conducted from 5° to 65° C. Usually the reaction is carried out in the presence of a suitable solvent which may include, but are not limited to water, methanol, ethanol, dioxane, tetrahydrofuran, acetic acid, t-butyl alcohol, isopropanol or mixtures thereof. The reaction is usually run at a positive hydrogen pressure of 50 psi but can be conducted over the range of 20 to 250 psi. Reactions are generally quantitative taking 1 to 24 hours for completion.

In any of the previous synthetic methods the desired products are preferably recovered from reaction mixtures by crystallization. Alternatively, normal or reverse-phase chromatography may be utilized as well as liquid/liquid extraction or other means.

The desired compounds of formula I are usually obtained in the free acid form; they may also be recovered as their physiologically acceptable salts, i.e., the corresponding amino salts such as hydrochloride, sulfate, hydrosulfate, nitrate, hydrobromide, hydroiodide, phosphate or hydrophosphate; or the alkali metal salts such as the sodium, potassium, lithium, or the alkaline earth metal salts such as calcium or magnesium, as well as aluminum, zinc and like salts.

Conversion of the free peptide derivatives of formula I into their physiologically acceptable salts is carried out by conventional means, as for example, bringing the compounds of formula I into contact with a mineral acid, an alkali metal hydroxide, an alkali metal oxide or carbonate or an alkaline earth metal hydroxide, oxide, carbonate or other complexed form.

These physiologically acceptable salts can also be utilized as sweetness agents usually having increased solubility and stability over their free forms.

The following examples further illustrate the invention.

EXAMPLE I

Preparation of L-aspartyl-O-(1-methylcyclopentyl)-L-serine methyl ester

A. N-Carbenzyloxy (CBZ)-L-serine methyl ester

N-CBZ-L-serine (25 g) was dissolved in 100 ml of dry N,N-dimethylformamide at 0° C. under argon. Triethylamine (2 e.g., 30 ml) and dimethylsulfate (20 ml) were added. The contents of the vessel were stirred overnight at room temperature and then poured into 500 ml of water and extracted with ethyl acetate (3×200 ml). The organic layer was washed with water and brine and dried with sodium sulfate. Rotary evaporation afforded an oil which crystallized after silica gel chromatography in pure ethyl ether. The structure of the product, N-CBZ-L-serine methyl ester, was confirmed by NMR spectroscopy.

B. N-CBZ-O-(1-methylcyclopentyl)-L-serine methylester.

N-CBZ-L-serine methyl ester (3.15 g) was dissolved in 40 ml of dichloromethane at 0° C. under argon. Methylenecyclopentane (20 ml) was added, followed by 16 drops of concentrated sulfuric acid. The contents of the vessel were stirred at room temperature overnight then poured into dilute aqueous sodium hydrogen carbonate and extracted with chlorofrom (2×30 ml). The organic layer was dried over sodium sulfate and evaporated. The residual oil was chromatographed on silica gel with 50/50 petroleum ether/diethyl ether to give an oil (78% yield). The product, N-CBZ-O-(1-methylycyclopentyl)-L-serine methyl ester, was confirmed by NMR spectroscopy.

C. 0-1-methylcyclopentyl-L-serine methyl ester

In a Paar hydrogenation bottle N-CBZ-O-(1-methylcyclopentyl)-L-serine methyl ester (2.7 g) was dissolved in methanol (50 ml) and purged with argon. Palladium on carbon (5%) (290 mg) was added and hydrogenation carried out at 50 psi. After cessation of hydrogen uptake the contents of the bottle were filtered through Celite and evaporated to give 1.65 g (93% yield) of the product.

D. N-CBZ-beta-benzyl-alpha-L-aspartyl-O-(1-methylcyclopentyl)-L-serine methyl ester O-(1-methylcyclopentyl)-L-serine methyl ester (1.65 g) was dissolved in N,N-dimethylformamide (96 ml) at 0° C. under argon. N-CBZ-alpha-L-aspartic acid-beta-benzyl ester (2.87 g) was added, followed by copper (II) chloride (1.08 g). Finally, dicyclohexylcarbodiimide (1.66 g) was added. The contents of the flask were stirred at room temperature over three hours and then poured into water (500 ml) and acidified to pH 5 with 2N hydrochloric acid. The product was extracted with (2×400 ml) ethyl acetate and dried over sodium sulfate. Rotary evaporation afforded an oil which was chromatographed on silica-gel with 2:1 petroleum ether/ethyl acetate to give an oil (3.4 g) (77% yield). The product N-CBZ-beta-benzyl -L-aspartyl-O-(1-methylcyclopentyl)-L-serine methyl ester was confirmed by mass spectrometry and NMR spectroscopy.

E. L-aspartyl-O-(1-methylcyclopentyl)-L-serine methyl ester

To a Paar hydrogenation bottle the N-CBZ-beta-benzyl ester protected peptide (2.5 g) was dissolved in absolute methanol (120 ml) and purged with argon. Palladium on carbon (5%) (300 mg) was added and hydrogenation carried out at 50 psi. After cessation of hydrogen uptake the contents of the bottle were filtered through Celite and evaporated to give a white solid (1.45 g) (99% yield).

Reverse phase chromatography on $C_{18}$ silica with 50% methanolic water gave pure L-aspartyl-O-(1-methylcyclopentyl)-L-serine methyl ester. Structure was confirmed by NMR spectroscopy and mass spectrometry.

The following sensory evaluations were obtained by a panel of experts using known weight percent aqueous solutions of the above compound matched to sucrose standard solutions as previously described.

| Concentration | Sucrose Equivalent |
|---|---|
| 0.005% | 2.5% |
| 0.010% | 5% |
| 0.025% | 10% |
| 0.05% | 12% |

It was further determined by the panel of experts that the sweetener possessed excellent temporal and sensory qualities.

EXAMPLE 2

L-aspartyl-O-(1-methylcyclohexyl)-L-serine methyl ester

This compound was prepared in an identical manner as disclosed in Example 1 except 1-methyl-1-cyclohexene was substituted for methylene cyclopentane.

The following sensory evaluations were obtained by a panel of experts using known weight percent aqueous solutions of the above compound matched to sucrose standard solutions as previously described.

| Concentration | Sucrose Equivalent |
|---|---|
| 0.005% | 2% |
| 0.010% | 4.5% |
| 0.025% | 8.5% |

EXAMPLE 3

L-aspartyl-O-(1-methylcyclobutyl)-L-serine methyl ester

This compound was prepared in an identical manner as described in Example 1 except methylenecyclobutane was substituted for methylene cyclopentane.

The following sensory evaluations were obtained by a panel of experts using known weight percent aqueous solutions of the above compound matched to sucrose standard solutions as previously described.

| Concentration | Sucrose Equivalent |
|---|---|
| 0.01% | 2% |
| 0.05% | 8% |

EXAMPLE 4

L-aspartyl-O-(cis-1,2-dimethylcyclohexyl)-L-serine methyl ester and
L-aspartyl-O-(trans-1,2-dimethylcyclohexyl)-L-serine methyl ester.

These compounds were prepared in an identical manner as described in Example 1 except 1,2-dimethyl-1-cyclohexene was substituted for methylenecyclopentane. The cis and trans isomers were separated after etherification by HPLC on silica using 6:1 hexane: ethyl acetate, carried through to end products, and evaluated separately.

The following sensory evaluations were obtained by a panel of experts using known weight percent aqueous solutions of the above compounds matched to sucrose standard solutions as previously described.

| Concentration | Sucrose Equivalent |
|---|---|
| CIS ISOMER | |
| 0.005% | 2.0% |
| 0.010% | 4.0% |
| 0.020% | 7.0% |
| TRANS ISOMER | |
| 0.005% | 1.5% |
| 0.010% | 3.0% |
| 0.020% | 5.0% |

EXAMPLE 5

L-aspartyl-O-(1-ethylcyclopentyl)-L-serine methyl ester

This compound was prepared in an identical manner as described in Example 1 except 1-ethyl-1-cyclopentene was substituted for methylenecyclopentane.

The following sensory evaluations were obtained as described.

| Concentration | Sucrose Equivalent |
|---|---|
| 0.005% | 2% |
| 0.01% | 4% |
| 0.02% | 6% |

EXAMPLE 6

Preparation of
α-L-aspartyl-O-(1-methylcyclopentyl)-L-threonine
methyl ester

A.
N-Carbenzyloxy(CBZ)-O-(1-methylcyclopentyl)-L-threonine methyl ester

N-CBZ-L-threonine methyl ester is etherified with 1-methylcyclopentene by using the same sulfuric acid catalyzed procedure as described in Example 1B, to afford the product.

B. N-CBZ-β-benzyl ester-α-L-aspartyl-O-(1-methylcyclopentyl)-L-threonine methyl ester O-(1-methylcyclopentyl)-L-threonine methyl ester (prepared by catalytic hydrogenation of N-CBZ-O-(1-methylcyclopentyl)-L-threonine methyl ester, as described in Example 1, C.), N-CBZ-alpha-L-aspartic acid-beta benzyl ester and N,N-dimethylformamide are added to a dry flask under argon at 0° C. Copper (II) chloride was next added. After the dissolution of the salt, dicyclohexylcarbodiimide is added. The contents of the flask are stirred at room temperature for 16 hours and poured into water (300 ml) and 0.1N hydrochloric acid (100 ml). The product is extracted with diethyl ether (3×100 ml) and is dried over sodium sulfate. Rotary evaporation affords an oil which is chromatographed over silica gel with 3:1 petroleum ether/ethyl acetate to give an oil of the diastereomeric products.

C. α-L-aspartyl-O-(1-methylcyclopentyl)-L-threonine methyl ester

The product from B is catalytically hydrogenated as described in Example 1E to afford the product.

EXAMPLE 7

Preparation of
L-aspartyl-O-(1-methylcyclohex-3-enyl)-L-serine
methyl ester

A. N-CBZ-O-(1-methylcyclohex-3-enyl)-L-serine methyl ester

This compound is prepared in an identical manner as disclosed in Example 1B, except 1-methyl-1,4-cyclohexadiene is substituted for methylene cyclopentane. The product is characterized by NMR spectroscopy.

B. O-1-methylcyclohex-3-enyl-L-serine methyl ester

The amino olefin was prepared by utilizing transfer hydrogenation rather than catalytic hydrogenation. The N-CBZ-O-(1-methylcyclohex-3-enyl)-L-serine methyl ester (691 mg, 2.2 mmol) was dissolved in absolute ethyl alcohol (9 ml) at 0° C. in an ultrasound bath. Palladium on carbon (10%) (695 mg) was added. The hydrogen source, 1,4-cyclohexadiene (2 ml, 20 equiv.) was added and ultrasound commenced for eight minutes. The slurry was then filtered through a bed of Celite with ethyl alcohol. Rotary evaporation affords an oil (382 mg, 98% yield) whose NMR spectrum indicates a free amine and cyclohexenyl moiety.

C. N-CBZ-β-benzyl-α-L-aspartyl-O-(1-methylcyclohex-3-enyl)-L-serine methyl ester The compound prepared in B above was reacted with N-CBZ-α-L-aspartic acid-β-benzyl ester in a manner as previously described in Example 1D, to afford the above product.

α-L-aspartyl-O-(1-methylcyclohex-3-enyl)-L-serine methyl ester

The protected dipeptide from the previous step (277 mg, 0.54 mmol) was dissolved in absolute ethyl alcohol (2 ml), and 10% palladium on carbon (240 mg) was added. The hydrogen source, 1,4-cyclohexadiene (1 ml, 10 equiv.), was added, and ultrasound commenced for five minutes. The slurry was then filtered through a bed of Celite with ethyl alcohol. Rotary evaporation afforded a white solid (158 mg).

EXAMPLE 8

A. N-CBZ-O-(1-(4-methylcyclohex-3-enyl)isopropyl)-L-serine methyl ester

The ether is prepared from N-CBZ-L-serine methyl ester and d-limonene in a manner similar to that described in Example 1B. The product can be characterized by NMR spectroscopy.

B. N-CBZ-β-benzyl ester-α-L-aspartyl-O-(1-(4-methylcyclohex-3-enyl)isopropyl)-L-serine methyl ester The amine olefin is prepared by transfer hydrogenation as described in Example 7B and coupled with N-CBZ-α-L-aspartic acid-β-benzyl ester by the copper mediated procedure as described in Example 1D.

C. α-L-aspartyl-O-(1-(4-methylcyclohex-3-enyl)isopropyl)-L-serine methyl ester The protected dipeptide is deprotected by transfer hydrogenation, as described in Example 7B, to give α-L-aspartyl-O-1-(4-methylcyclohex-3-enyl)isopropyl)-L-serine methyl ester.

D. α-L-aspartyl-O-(1-(cis-4-methylcyclohexyl)isopropyl)-L-serine methyl ester The product of B above is deprotected by catalytic hydrogenation in a manner as described in Example 1E to afford the above compound.

The following sensory evaluations were obtained by a panel of experts using known weight percent aqueous solutions of the above compound matched to sucrose standard solutions as previously described:

| Sensory Evaluations | |
|---|---|
| Concentrations | Sucrose Equivalent |
| 0.01 | 2.2 |
| 0.025 | 5.2 |

EXAMPLE 9

Preparation of DL-2-amino
malonyl-O-(1-methylcyclopentyl)-L-serine methyl
ester

A. N-CBZ-DL-2-amino malonic acid mono benzyl ester

Dibenzyl malonate (10.0 g, 35.2 mmol) was taken up in 1,4-dioxane (100 mL) and treated with a 40% aqueous solution of acetic acid (35 mL), followed by the slow addition (2.5 h) of solid sodium nitrite (10 g). The reaction was stirred for another 2.5 h and extracted into ether (3×70 mL). The organic phase was washed with a 1% solution of NaHCO$_3$ until the aqueous layer was slightly acidic (pH 5-6). The ethereal solution was dried over MgSO$_4$ and removed under reduced pressure to give an oil (10.9 g). The crude oxime was carried directly to the next step.

Amalgamated aluminum (obtained from 1.25 g, 0.463 g atom of aluminum foil) was covered with tetrahydrofuran (28 mL) followed by 1.9 mL of water. The reaction mixture was stirred mechanically and cooled in a dry ice acetone bath. A solution of the crude oxime (from the previous step) in 30 mL of tetrahydrofuran was added dropwise (20 min.) while the temperature was maintained between −15° and −30° C. The ice bath was removed and spontaneous reaction occurred, which resulted in a rapid rise in temperature (50°0 C. ). When the evolution of heat ceased, the mixture was refluxed for 1 hour, diluted with ether (100 mL) and filtered through Celite. The solvent was removed under reduced pressure to give the crude amine (7.5 g), which was taken to the following step without further purification. The crude amine (7 g) was dissolved in a saturated solution of NaHCO$_3$ (200 mL) and cooled in an ice bath. Benzyl chloroformate (4.0 g, 23 mmol) was added dropwise (0.5 h) to the vigorously stirred solution. The reaction mixture was left at room temperature for 12 hours, during which time the product precipitated. The product was collected by filtration, washed with water, dried in air, and recrystallized from i-PrOH: yield 4.8 g (52%) from dibenzyl malonate; m.p. 104°–106° C.

N-(benzyloxycarbonyl)-2-amino malonic acid dibenzyl ester (4.33 g, 10 mmol) was dissolved in acetone/water (4.1, 133 mL). The solution was stirred and lithium hydroxide monohydrate (0.42 g, 10 mmol) in water (11 mL) was added dropwise (1 h). The reaction mixture was stirred for 12 hours at room temperature, the acetone was removed under reduced pressure, and the residue was taken up into a saturated solution of NaHCO$_3$ (60 mL) and extracted with EtOAc (3×100 ml). The EtOAc washings were combined, dried over MgSO$_4$ and removed under reduced pressure to give a solid, which was crystallized from EtOAc/hexane. This solid was identified as recovered starting material (1.1 g, 25.4%). The aqueous phase was acidified with 3 N HCl to pH=1 and extracted with CHCl$_3$ (4×50 mL). The combined CHCl$_3$ washings were dried over MgSO$_4$ and the solvent was removed under reduced pressure to give a residue which crystallized from i-PrOH: yield 2.0 g (58%); m.p. 114°–116° C.

B. N-CBZ-DL-2-amino malonyl benzyl ester-O-1-methylcyclopentyl)-L-serine methyl ester The mono carboxylic acid from the last step of Section A (2 g, 5.83 mmol) was dissolved in dry acetonitrile (75 ml) at 0° C. under argon. Then, O-(1-methylcyclopentyl)-L-serine methyl ester, (1.2 g, 1 equiv.) was added, as described in Example 1D. Lastly, dicyclohexylcarbodiimide (1.2 g, 1 equiv.) was added and the contents of the flasks were stirred at room temperature.

The reaction mixture was rotary evaporated to remove the acetonitrile and the residue was taken up in 0.1N hydrochloric acid (100 ml) and extracted with diethyl ether (3×100 ml). The ethereal layer was dried over sodium sulfate and filtered to remove insoluble urea. The ether is removed by rotary evaporation. The coupled product was purified by silica gel chromatography with 3:1 petroleum ether/ethyl acetate.

C. DL-2-amino malonyl-O-(1-methylcyclopentyl)-L-serine methyl ester

The bis-protected dipeptide from Section B was dissolved in absolute methanol under argon. 10% Palladium on carbon was added and hydrogenation was carried out at 50 psi. After cessation of hydrogen uptake, the mixture was filtered through Celite and rotary evaporated to give a white solid.

EXAMPLE 10

α-L-Aspartyl-O-2,2,5,5-tetramethylcyclopentyl-L-serine methyl ester

A. L-N-Triphenylmethyl serine methyl ester

A solution of L-serine methyl ester hydrochloride (100 g), triphenylmethylchloride (179.3 g) and triethylamine (197 ml) was stirred at 0° C. for 2 hours, then allowed to warm to room temperature overnight. The solution was then washed successively with 10% aqueous citric acid and water, dried over magnesium sulfate, and the solvent was evaporated to yield 212 g of the product (91% yield).

B. L-1-Triphenylmethyl-aziridine-2-carboxylic acid methyl ester

A mixture of compound A (212 g), methanesulfonyl chloride (45.6 ml), and pyridine (1.76 l) was stirred at 0° C., then allowed to warm slowly to room temperature overnight. Ethyl acetate (1.5 l) was added, and the resulting solution was washed with 10% aqueous citric acid and water, dried over magnesium sulfate and the solvent was removed. The residual oil was dissolved in tetrahydrofuran (2.5 l) and a triethylamine (143 ml) was added. The mixture was heated at reflux overnight. The solution was then cooled, and most of the solvent was removed under vacuum. The residual oil was dissolved in ethyl acetate (2 l) and the solution was washed successively with 10% aqueous citric acid, saturated aqueous sodium bicarbonate, and water, was dried over magneisum sulfate, and the solvent was evaporated under vacuum. The residue was dissolved in hot methanol (300 ml). Upon cooling, compound B crystallized as an off-white powder which was removed by filtration and then air dried (115 g), (57% yield). The structure was confirmed by NMR. $[\alpha]^{25}_D = -90.5°$ (±0.5) (C 1.0 THF).

C. L-1-Benzyloxycarbonylaziridine-2-carboxylic acid methyl ester

To a cold solution (0° C.) of compound B (17.0 g) and methanol (100 ml) in dichloromethane (100 ml) was added concentrated sulfuric acid (5.0 ml). The mixture was stirred at 0° for 10 min. Approximately half of the solvent was removed under vacuum, and the residue was dissolved in ether. This solution was extracted with water. The aqueous extract was made basic with sodium bicarbonate and extracted with dichloromethane (3×25 ml). To these combined extracts was added triethylamine (4.63 g) and the solution was cooled to 0°. Benzyl chloroformate (7.80 g), was added, and the mixture was allowed to warm to room temperature overnight. The solution was then washed successively with 1M aqueous hydrochloric acid and saturated aqueous sodium bicarbonate, dried over magnesium sulfate, and the solvent was removed under vacuum to yield a brown oil (7.0 g). The product was purified by column chromatography on silica gel (4:1 hexanes:ethyl acetate, eluent) to yield compound C (3.44 g, 30%) as a slightly yellow oil.

D. N-Benzyloxycarbonyl-O-2,2,5,5-tetramethylcyclopentyl-L-serine methyl ester To a solution of compound C (1.00 g) and 2,2,5,5-tetramethylcyclopentanol (1.2 g) in dichloromethane (20 ml) was added boron trifluoride diethyl etherate (15 drops). The mixture was stirred at room temperature for 4 hours, then washed with water, dried over magnesium sulfate and the solvent was evaporated. The residue was purified by column chromatography (silica gel, 10:1, hexanes: ethyl acetate, eluent) to yield compound D as a colorless oil (0.34 g, 21% yield).

E. O-2,2,5,5-Tetramethylcyclopentyl-L-serine methyl ester

Compound D (0.34 g) was deprotected by the usual procedure to yield compound E (0.214 g, 98% yield).

F. N-Benzyloxycarbonyl-α-L-aspartyl-β-benzyl ester-O-2,2,5,5-tetramethylcyclopentyl-L-serine methyl ester Compound E (0.214 g) was coupled with N-benzyloxy carbonyl-L-aspartic acid-β-benzyl ester (0.33 g) by the copper (II) chloride procedure to yield compound F (0.300 g, 60% yield).

G. α-L-Aspartyl-O-(2,2,5,5-tetramethylcyclopentyl)-L-serine methyl ester

Compound F (0.300 g) was deprotected by the usual procedure to yield compound G (0.090 g, 43% yield).

Using appropriate starting materials in this procedure, the following compounds are prepared:

α-L-aspartyl-O-2,2,6,6-tetramethylcyclohexyl-L-serine methyl ester
α-L-aspartyl-O-1,2,7-trimethylcycloheptyl-L-serine methyl ester
α-L-aspartyl-O-1,2,2-trimethylcycloheptyl-L-serine methyl ester
α-L-aspartyl-O-2,2,7,7-tetramethylcycloheptyl-L-serine methyl ester
α-L-aspartyl-[O-(2,2,3,3-tetramethylcyclopropyl)]-L-serine methyl ester
α-L-aspartyl-[O-(2,2,4,4-tetramethylcyclobutyl)]-L-serine methyl ester
α-L-aspartyl-[O-(2,2,5-trimethylcyclopentyl)]-L-serine methyl ester
α-L-aspartyl-[O-(2,5-dimethylcyclopentyl)]-L-serine methyl ester
α-L-aspartyl-O-2-methylcyclohexyl-L-serine methyl ester
α-L-aspartyl-O-cyclohexyl-L-serine methyl ester
α-L-aspartyl-O-cyclopentyl-L-serine methyl ester
α-L-aspartyl-O-cyclobutyl-L-serine methyl ester
α-L-aspartyl-O-(2,2,6-trimethylcyclohexyl)-L-serine methyl ester
α-L-aspartyl-O-(2-ethylcyclopentyl)-L-serine methyl ester
α-L-aspartyl-O-(2-isopropylcyclohexyl)-L-serine methyl ester
α-L-aspartyl-O-(2-t-butylcyclopropyl)-L-serine methyl ester
α-L-aspartyl-O-(2,2,6-trimethylnorbornyl)-L-serine methyl ester
α-L-aspartyl-[O-(2,2-dimethylcyclopentyl)]-L-serine methyl ester
α-L-aspartyl-[O-(2,2-dimethylcyclohexyl)]-L-serine methyl ester
α-L-aspartyl-[O-(2,2,4,4-tetramethylcyclobutyl)]-L-serine methyl ester
α-L-aspartyl-[O-(2-methylcyclopentyl) -L-serine methyl ester
α-L-aspartyl-[O-(2-methylcyclohexyl)]-L-serine methyl ester
α-L-aspartyl-[O-(2-isopropylcyclopentyl)]-L-serine methyl ester
α-L-aspartyl-[O-(2-isopropylcyclohexyl)]-L-serine methyl ester
α-L-aspartyl-[O-(2-t-butylcyclopentyl)]-L-serine methyl ester
α-L-aspartyl-[O-(2t-butylcyclohexyl)]-L-serine methyl ester
α-L-aspartyl-[O-(dicyclopropylmethyl)]-L-serine methyl ester
α-L-aspartyl-[O-(dicyclobutylmethyl)]-L-serine methyl ester
α-L-aspartyl-[O-(t-butylcyclopropylmethyl)]-L-serine methyl ester
α-L-aspartyl-[O-(t-butylcyclobutylmethyl)]-L-serine methyl ester
α-L-aspartyl-[O-(fenchyl)]-L-serine methyl ester
α-L-aspartyl-[O-(benzyl)]-L-serine methyl ester
α-L-aspartyl-[O-(α-methylbenzyl)]-L-serine methyl ester
α-L-aspartyl-[O-(o-methylbenzyl)]-L-serine methyl ester
α-L-aspartyl-[O-(2-furylmethyl)]-L-serine methyl ester
α-L-aspartyl-[O-(3-furylmethyl)]-L-serine methyl ester
α-L-aspartyl-[O-2-(5-methylfuryl)methyl]-L-serine methyl ester
α-L-aspartyl-[O-(2-thienylmethyl)]-L-serine methyl ester
α-L-aspartyl-[O-(3-thienylmethyl)]-L-serine methyl ester
α-L-aspartyl-[O-2-(5-methylthienyl)methyl]-L-serine methyl ester

EXAMPLE 11

α-L-Aspartyl-O-1-bornyl-L-serine methyl ester

This compound was prepared in an identical manner as described in Example 1 except camphene was substituted for methylenecyclopentane.

Similarly, α-L-Aspartyl-O-1-norbornyl-L-serine methyl ester and α-L-Aspartyl-O-[2-(4-norbornenyl)ethyl]-L-serine methyl ester were prepared using norbornene and ethylidenylnorbornene, respectively.

α-L-Aspartyl-O-2-norbornylethyl-L-serine methyl ester was prepared by the catalytic hydrogenation of -L-Aspartyl-O-[2-(4-norbornenyl)ethyl]-L-serine methyl ester.

EXAMPLE 12

α-L-Aspartyl-O-(1-methyl-cycloheptyl)-L-serine methyl ester

Using the same procedure as disclosed in Example 1 and substituting 1-methyl-1-cycloheptene for methylene cyclopentane, α-L-aspartyl-O-(1-methylcycloheptyl)-L-serine methyl ester was prepared.

EXAMPLE 13

α-L-Aspartyl-O-cyclopentyl-L-serine methyl ester

This compound is prepared according to the method as described in Example 10, except cyclopentanol is substituted for 2,2,5,5-tetramethylcyclopentanol.

EXAMPLE 14

Preparation of L-aspartyl-S-(1-methylcyclohex-3-enyl)-L-cysteine methyl ester

A. N-CBZ-S-(1-methylcyclohex-3-enyl)-L-cysteine methyl ester

This compound is prepared in an identical manner as disclosed in Example 1B, except 1-methyl-1,4-cyclohexadiene is substituted for methylene cyclopentane. The product is characterized by NMR spectroscopy.

B. S-1-methylcyclohex-3-enyl-L-cysteine methyl ester

The amino olefin was prepared by utilizing transfer hydrogenation rather than catalytic hydrogenation. The N-CBZ-S-(1-methylcyclohex-3-enyl)-L-cysteine methyl ester (691 mg, 2.2 mmol) was dissolved in absolute ethyl alcohol (9 ml) at 0° C. in an ultrasound bath. Palladium on carbon (10%) (695 mg) was added. The hydrogen source, 1,4-cyclohexadiene (2 ml, 20 equiv.) was added and ultrasound commenced for eight minutes. The slurry was then filtered through a bed of Celite with ethyl alcohol. Rotary evaporation affords an oil (382 mg, 98% yield) whose NMR spectrum indicates a free amine and cyclohexenyl moiety.

C. N-CBZ-β-benzyl-α-L-aspartyl-S-(1-methylcyclohex-3-enyl)-L-cysteine methyl ester The compound prepared in B above was reacted with N-CBZ-α-L-aspartic acid-β-benzyl ester in a manner as previously described in Example 1D, to afford the above product.

D. α-L-aspartyl-S-(1-methylcyclohex-3-enyl)-L-cysteine methyl ester

The protected dipeptide from the previous step (277 mg, 0.54 mmol) was dissolved in absolute ethyl alcohol (2 ml), and 10% palladium on carbon (240 mg) was added. The hydrogen source, 1,4-cyclohexadiene (1 ml, 10 equiv.), was added, and ultrasound commenced for five minutes. The slurry was then filtered through a bed of Celite with ethyl alcohol. Rotary evaporation afforded a white solid (1.58 mg).

EXAMPLE 15

A. N-CBZ-S-(1-(4-methylcyclohex-3-enyl)isopropyl)-L-cysteine methyl ester

The ether is prepared from N-CBZ-L-cysteine methyl ester and α-limonene in a manner similar to that described in Example 1B. The product can be characterized by NMR spectroscopy.

B. N-CBZ-B-benzyl ester-α-L-aspartyl-S-(1-(4-methylcyclohex-3-enyl)isopropyl)-L-cysteine methyl ester The amine olefin is prepared by transfer hydrogenation as described in Example 7B and coupled with N-CBZ-α-L-aspartic acid-β-benzyl ester by the copper mediated procedure as described in Example 1D.

C. α-L-aspartyl-O-1-(4-(methylcyclohex-3-enyl)isopropyl)-L-cysteine methyl ester The protected dipeptide is deprotected by transfer hydrogenation, as described in Example 7B to give α-L-aspartyl-S-1-(4-methylcyclohex-3-enyl)isopropyl)-L-cysteine methyl ester.

D. α-L-aspartyl-S-(1-(cis-4-methylcyclohexyl)isopropyl)-L-cysteine methyl ester The product of B above is deprotected by catalytic hydrogenation in a manner as described in Example 1E to afford the above compound.

EXAMPLE 16

Preparation of DL-2-amino malonyl-S-(1-methylcyclopenyl)-L-cysteine methyl ester

A. N-CBZ-DL-2-amino malonic acid mono benzyl ester

Dibenzyl malonate (10.0 g, 35.2 mmol) was taken up in 1,4-dioxane (100 mL) and treated with a 40% aqueous solution of acetic acid (35 mL), followed by the slow addition (2.5 h) of solid sodium nitrate (10 g). The reaction was stirred for another 2.5 h and extracted into ether (3×70 mL). The organic phase was washed with a 1% solution of NaHCO₃ until the aqueous layer was slightly acidic (pH 5-6). The ethereal solution was dried over MgSO₄ and removed under reduced pressure to give an oil (10.9 g). The crude oxime was carried directly to the next step.

Amalgamated aluminum (obtained from 1.25 g, 0.463 g atom of aluminum foil) was covered with tetrahydrofuran (28 mL) followed by 1.9 mL of water. The reaction mixture was stirred mechanically and cooled in a dry ice acetone bath. A solution of the crude oxime (from the previous step) in 30 mL of tetrahydrofuran was added dropwise (20 min.) while the temperature was maintained between −15° and −30° C. The ice bath was removed and spontaneous reaction occurred, which resulted in a rapid rise in temperature (50° C.). When the evolution of heat ceased, the mixture was refluxed for 1 hour, diluted with ether (100 mL) and filtered through Celite. The solvent was removed under reduced pressure to give the crude amine (7.5 g), which was taken to the following step without further purification. The crude amine (7 g) was dissolved in a saturated solution of NaHCO₃ (200 mL) and cooled in an ice bath. Benzyl chloroformate (4.0 g, 23 mmol) was added dropwise (0.5 h) to the vigorously stirred solution. The reaction mixture was left at room temperature for 12 hours, during which time the product precipitated. The product was collected by filtration, washed with water, dried in air, and recrystallized from i-PrOH: yield 4.8 g (52%) from dibenzyl malonate; m.p. 104°-106° C.

N-(benzyloxycarbonyl)-2-amino malonic acid dibenzyl ester (4.33 g, 10 mmol) was dissolved in acetone/water (4.1, 133 mL). The solution was stirred and lithium hydroxide monohydrate (0.42 g, 10 mmol) in water (11 mL) was added dropwise (1 h). The reaction mixture was stirred for 12 hours at room temperature, the acetone was removed under reduced pressure, and the residue was taken up into a saturated solution of NaHCO₃ (60 mL) and extracted with EtOAc (3×100 ml).

The EtOAc washings were combined, dried over MgSO4 and removed under reduced pressure to give a solid, which was crystallized from EtOAc/hexane. This solid was identified as recovered starting material (1.1 g, 25.4%). The aqueous phase was acidified with 3N HCl to pH=1 and extracted with CHCl3 (4×50 mL). The combined CHCl3 washings were dried over MgSO4 and the solvent was removed under reduced pressure to give a residue which crystallized from i-PrOH: yield 2.0 g (58%); m.p. 114°–116° C.

B. N-CBZ-DL-2-amino malonyl benzyl ester-S-1-methylcyclopentyl)-L-cysteine methyl ester The mono-carboxylic acid from the last step of Section A (2 g, 5.83 mmol) was dissolved in dry acetonitrile (75 ml) at 0° C. under argon. Then, S-(1-methylcyclopentyl)-L-cysteine methyl ester (1.2 g, 1 equiv.) was added, as described in Example 1D. Lastly, dicyclohexylcarbodiimide (1.2 g, 1 equiv.) was added and the contents of the flasks were stirred at room temperature.

The reaction mixture was rotary evaporated to remove the acetonitrile and the residue was taken up in 0.1N hydrochloric acid (100 ml) and extracted with diethyl ether (3×100 ml). The ethereal layer was dried over sodium sulfate and filtered to remove insoluble urea. The ether is removed by rotary evaporation. The coupled product was purified by silica gel chromatography with 3:1 petroleum ether/ethyl acetate.

C. DL-2-amino malonyl-S-(1-methylcyclopentyl)-L-cysteine methyl ester

The bis-protected dipeptide from Section B was dissolved in absolute methanol under argon. 10% Palladium on carbon was added and hydrogenation was carried out at 50 psi. After cessation of hydrogen uptake, the mixture was filtered through Celite and rotary evaporated to give a white solid.

EXAMPLE 17

L-Aspartyl-S-2,2,5,5-tetramethylcyclopentyl-L-cysteine methyl ester

A. L-N-Triphenylmethyl cysteine methyl ester

A solution of L-cysteine methyl ester hydrochloride (100 g), triphenyl chloride (179.3 g) and triethylamine (197 ml) was stirred at 0° C. for 2 hours, then allowed to warm to room temperature overnight. The solution was then washed successively with 10% aqueous citric acid and water, dried over magnesium sulfate, and the solvent was evaporated to yield 212 g of the product (91% yield).

B. L-1-Triphenyl methyl aziridine-2-carboxylic acid methyl ester

A mixture of compound A (212 g), methanesulfonyl chloride (45.6 ml), and pyridine (1.76 l) was stirred at 0°, then allowed to warm slowly to room temperature overnight. Ethyl acetate (1.5 l) was added, and the resulting solution was washed with 10% aqueous citric acid and water, dried over magnesium sulfate and the solvent was removed. The residual oil was dissolved in tetrahydrofuran (2.5 l) and a triethylamine (143 ml) was added. The mixture was heated at reflux overnight. The solution was then cooled, and most of the solvent was removed under vacuum. The residual oil was dissolved in ethyl acetate (2 l) and the solution was washed successively with 10% aqueous citric acid, saturated aqueous sodium bicarbonate, and water, was dried over magnesium sulfate, and the solvent was evaporated under vacuum. The residue was dissolved in hot methanol (300 ml). Upon cooling, compound B crystalized as an off-white powder which was removed by filtration and then air dried (115 g), (57% yield). The structure was confirmed by NMR. $[\alpha]_D = -90.5° \pm 0.5$ (C 1.0 THF).

C. L-1-Benzyloxycarbonylaziridine-2-carboxylic acid methyl ester

To a cold solution (0°) of compound B (17.0 g) and methanol (100 ml) is dichloromethane (100 ml) was added concentrated sulfuric acid (5.0 ml). The mixture was stirred at 0° for 10 min. Approximately half of the solvent was removed under vacuum, and the residue was dissolved in ether. This solution was extracted with water. The aqueous extract was made basic with sodium bicarabonate and extracted with dichloromethane (3×25 ml). To these combined extracts was added triethylamine (4.63 g) and the solution was cooled to 0°. Benzyl chloroformate (7.80 g), was added, and the mixture was allowed to warm to room temperature overnight. The solution was then washed successively with 1M aqueous hydrochloric acid and saturated aqueous sodium bicarbonate, dried over magnesium sulfate, and the solvent was removed under vacuum to yield a brown oil (7.0 g). The product was purified by column chromatography on silica gel (4:1 hexanes:ethyl acetate, eluent) to yield compound C (3.44 g, 30%) as a slightly yellow oil.

D. N-Benzyloxycarbonyl-S-2,2,5,5-tetramethylcyclopentyl-L-cysteine methyl ester To a solution of compound C (1.00 g) and 2,2,5,5-tetramethylcyclopentanol (1.2 g) in dichloromethane (20 ml) was added boron trifluoride diethyl ethereate (15 drops). The mixture was stirred at room temperature for 4 hours, then washed with water, dried over magnesium sulfate and the solvent was evaporated. The residue was purified by column chromatography (silica gel, 10:1, hexanes:ethyl acetate, eluent) to yield compound D as a colorless oil (0.34 g, 21% yield).

E. S-2,2,5,5-Tetramethylcyclopentyl-L-cysteine methyl ester

Compound D (0.34 g) was deprotected by the usual procedure to yield compound E (0.214 g, 98% yield).

F. N-Benzyloxycarbonyl-α-L-aspartyl-β-benzyl ester-S-2,2,5,5-tetramethylcyclopentyl-L-cysteine methyl ester Compound E (0.214 g) was coupled with N-benzyloxy carbonyl-L-aspartic acid-β-benzyl ester (0.33 g) by the copper (II) chloride procedure to yield compound F (0.300 g, 60% yield).

G. α-L-Aspartyl-S-2,2,5,5-tetramethylcyclopentyl-L-cysteine methyl ester

Compound F (0.300 g) was deprotected by the usual procedure to yield compound G (0.090 g, 43% yield).

Using appropriate starting materials, the following compounds are prepared:

α-L-aspartyl-S-2,2,6,6-tetramethylcyclohexyl-L-cysteine methyl ester

α-L-aspartyl-S-1,2,7-trimethylcycloheptyl-L-cysteine methyl ester

α-L-aspartyl-S-1,2,2-trimethylcycloheptyl-L-cysteine methyl ester
α-L-aspartyl-S-2,2,7,7-tetramethylcycloheptyl-L-cysteine methyl ester α-L-aspartyl-[S-(2,2,3,3-tetramethylcyclopropyl)]-L-cysteine methyl ester
α-L-aspartyl-[S-(2,2,4,4-tetramethylcyclobutyl)]-L-cysteine methyl ester
α-L-aspartyl-[S-(2,2,5-trimethylcyclopentyl)]-L-cysteine methyl ester
α-L-aspartyl-[S-(2,5-dimethylcyclopentyl)]-L-cysteine methyl ester
α-L-aspartyl-[S-(2,2-dimethylcyclopentyl)]-L-cysteine methyl ester
α-L-aspartyl-[S-(2,2-dimethylcyclohexyl)]-L-cysteine methyl ester
α-L-aspartyl-[S-(2,2,4,4-tetramethylcyclobutyl)]-L-cysteine methyl ester
α-L-aspartyl-[S-(2-methylcyclopentyl)]-L-cysteine methyl ester
α-L-aspartyl-[S-(2-methylcyclohexyl)]-L-cysteine methyl ester
-L-aspartyl-[S-(2-issopropylcyclopentyl)]-L-cysteine methyl ester α-L-aspartyl-[S-(2-isopropylcyclohexyl)]-L-cysteine methyl ester
α-L-aspartyl-[S-(2-t-butylcyclopentyl)]-L-cysteine methyl ester
α-L-aspartyl-[S-(2-t-butylcyclohexyl)]-L-cysteine methyl ester
α-L-aspartyl-[S-(dicyclopropylmethyl)]-L-cysteine methyl ester
α-L-aspartyl-[S-(dicyclobutylmethyl)]-L-cysteine methyl ester
α-L-aspartyl-[S-(t-butylcyclopropylmethyl)]-L-cysteine methyl ester
α-L-aspartyl-[S-(t-butylcyclobutylmethyl)]-L-cysteine methyl ester
α-L-aspartyl-[S-(fenchyl)]-L-cysteine methyl ester
α-L-aspartyl-[S-(benzyl)]-L-cysteine methyl ester
α-L-aspartyl-[S-(α-methylbenzyl)]-L-cysteine methyl ester
α-L-aspartyl-[S-(o-methylbenzyl)]-L-cysteine methyl ester
α-L-aspartyl-[S-(2-furylmethyl)]-L-cysteine methyl ester
α-L-aspartyl-[S-(3-furylmethyl)]-L-cysteine methyl ester
α-L-aspartyl-[S-2-(5-methylfuryl)methyl]-L-cysteine methyl ester
α-L-aspartyl-[S-(2-thienylmethyl)]-L-cysteine methyl ester
α-L-aspartyl-[S-(3-thienylmethyl)]-L-cysteine methyl ester
α-L-aspartyl-[S-2-(5-methylthienyl)methyl]-L-cysteine methyl ester

EXAMPLE 18

α-L-Aspartyl-S-cyclopentyl-L-cysteine methyl ester

This compound is prepared according to the method as described in Example 23, except cyclopentanol is substituted for 2,2,5,5-tetramethylcyclopentanol.

EXAMPLE 19

α-L-aspartyl-S-(1-methyl-cycloheptyl)-L-cysteine methyl ester and α-L-aspartyl-S-cyclopentyl-L-cysteine methyl ester Using the same procedure as disclosed in Example 1 and substituting 1-methyl-1-cycloheptene for methylene cyclopentane, α-L-aspartyl-S-(1-methylcycloheptyl)-L-cysteine methyl ester was prepared.

Similarly, by using cyclopentene, α-L-aspartyl-S-cyclopentyl-L-cysteine methyl ester was prepared.

EXAMPLE 20

A. N-CBZ-L-cysteine ethyl ester

Thionyl chloride (5.25 mL, 72 mmol, 3.6 equiv.) is added dropwise to a 0° C. solution of absolute ethyl alcohol (20 ml). Diisopropyl ethylamine (3.45 ml, 19 mmol, 1 equiv.) was added as a solid. Stirring is continued for 16 hours at room temperature. The ethanol and thionyl chloride are then removed by rotary evaporation and the residue is dissolved in ethyl acetate (200 ml). The organic phase is washed with 1N hydrochloric acid (50 ml) and saturated sodium bicarbonate (50 ml) and brine (20 ml). The product is dried with magnesium sulfate. Rotary evaporation of the product gave an oil which was chromatographed on silica gel with hexane/ethyl acetate (3:1) to give N-CBZ-L-cysteine ethyl ester.

The carbenzyloxy group was removed by the procedure as described in Example 1, C.

Using the above starting material, the ethyl esters of the compounds of the foregoing examples are prepared.

EXAMPLE 21

L-α-Aspartyl-O-(dicyclopropylmethyl)-L-serine methyl ester

This compound is prepared in accordance with the procedure of Example 10, employing dicyclopropylmethanol as the alcohol starting material in lieu of 2,2,5,5-tetramethylcyclopentanol.

Similarly prepared from corresponding alcohols using this procedure are:
L-α-aspartyl-O-(cyclopropylcyclopentylmethyl)-L-serine methyl ester
L-α-aspartyl-O-(cyclopropyl-2-methylcyclohexylmethyl)-L-serine methyl ester
L-α-aspartyl-O-(cyclopentyl-2,5-dimethylcyclopentylmethyl)-L-serine methyl ester
L-α-aspartyl-O-(cyclobutyl-2,2,6,6-tetramethylcyclohexylmethyl)-L-serine methyl ester
L-α-aspartyl-O-(dicyclopentylmethyl)-L-serine methyl ester
L-α-aspartyl-O-(t-butylcyclopropylmethyl)-L-serine methyl ester
L-α-aspartyl-O-(t-butylcyclopentylmethyl)-L-serine methyl ester

EXAMPLE 22

L-α-Aspartyl-S-(dicyclopropylmethyl)-L-cystein methyl ester

This compound is prepared in accordance with the procedure of Example 10, employing dicyclopropylmethanol as the alcohol starting material in lieu of 2,2,5,5-tetramethylcyclopentanol.

Similarly prepared from corresponding alcohols using this procedure are:
L-α-aspartyl-S-(cyclopropylcyclopentylmethyl)-L-cysteine methyl ester
L-α-aspartyl-S-(cyclopropyl-2-methylcyclohexylmethyl)-L-cysteine methyl ester
L-α-aspartyl-S-(cyclopentyl-2,5-dimethylcyclopentylmethyl)-L-cysteine methyl ester L-α-aspartyl-S-(cyclobutyl-2,2,6,6-tetramethylcyclohexylmethyl)-L-cysteine methyl ester L-α-aspartyl-S-(dicyclopentylmethyl)-L-cysteine methyl ester

EXAMPLE 23

L-α-Aspartyl-O-phenyl-L-serine methyl ester

This compound is prepared in accordance with the procedure of Example 10, employing phenol as the alcohol starting material in lieu of 2,2,5,5-tetramethylcyclopentanol.

Similarly prepared from corresponding alcohols using this procedure are:

L-α-aspartyl-O-(2,6-dimethylphenyl)-L-serine methyl ester

L-α-aspartyl-O-(3,5-dimethylphenyl)-L-serine methyl ester

L-α-aspartyl O-(2-methylphenyl)-L-serine methyl ester

L-α-aspartyl-O-benzyl-L-serine methyl ester

EXAMPLE 24

L-α-Aspartyl-S-phenyl-L-cysteine methyl ester

This compound is prepared in accordance with the procedure of Example 10, employing phenol as the alcohol starting material in lieu of 2,2,5,5-tetramethylcyclopentanol.

Similarly prepared from corresponding alcohols using this procedure are:

L-α-aspartyl-S-(2,6-dimethylphenyl)-L-cysteine methyl ester

L-α-aspartyl-S-(3,5-dimethylphenyl)-L-cysteine methyl ester

L-α-aspartyl-S-(2-methylphenyl)-L-cysteine methyl ester

EXAMPLE 25

Preparation of acid salts

The dipeptides described in the preceding examples are converted to acid salts, e.g., hydrochlorides, by dissolving in an aqueous solution containing an equivalent amount of acid, e.g., hydrochloric acid, and the solution is evaporated to dryness to obtain the solid salt. Alternatively, alcholic solutions of hydrogen chloride gas, e.g., HCl, dissolved in ethanol can be used in lieu of the aqueous acid solution and the acid salt obtained by evaporation of solvent or crystallization from the alcohol, e.g., by addition of a non-solvent.

Metal salts of the peptides of the preceding examples are prepared by dissolving an equivalent amount of the selected metal compound, e.g, $Na_2CO_3$, $K_2CO_3$ or CaO, in water, dissolving the dipeptide in the resulting solution and evaporation of the resulting aqueous solution to dryness.

EXAMPLE 26

The following cyclic ethers are prepared from the corresponding ethylenically unsaturated compounds or the corresponding alcohol $R_1(CR_5R_6)_nOH$ using the respective procedures of the preceding examples.

α-L—Aspartyl-NH—CHCO$_2$R
           |
           CHO(CR$_5$R$_6$)$_n$R$_1$
           |
           R$_3$

| $R_1$ | n | R | $R_3$ | $R_5$ | $R_6$ |
|---|---|---|---|---|---|
| pyranyl | 0 | Me | H | — | — |
| 3-tetrahydrofuryl | 0 | Me | H | — | — |
| 3-tetrahydrofuryl | 1 | Me | H | H | H |
| pyranyl | 1 | Me | H | cyclopropyl | H |
| 2-methylfuryl | 1 | Me | H | H | H |
| 2-methylfuryl | 1 | Me | H | cyclopropyl | H |
| 3-(4,5-dihydrofuryl) | 1 | Me | H | H | H |
| 3-(4,5-dihydrofuryl) | 2 | Me | H | H | H |
| 3-(2,2,4,4-tetramethyltetrahydrofuryl) | 0 | Me | H | — | — |
| 3-(2,2,4-trimethyltetrahydrofuryl) | 0 | Me | H | — | — |
| 3-(2,4-dimethyltetrahydrofuryl) | 0 | Me | H | — | — |
| 3-(2,2-dimethyltetrahydrofuryl) | 0 | Me | H | — | — |
| 3-(4,4-dimethyltetrahydrofuryl) | 0 | Me | H | — | — |
| 3-(2,2,4,4-tetramethyltetrahydropyranyl) | 0 | Me | H | — | — |
| 4-(3,3,5,5-tetramethyltetrahydropyranyl) | 0 | Me | H | — | — |
| 4-(3,3,5-trimethyltetrahydropyranyl) | 0 | Me | H | — | — |
| 4-(3,5-dimethyltetrahydropyranyl) | 0 | Me | H | — | — |
| 3-(2,2,4-trimethyltetrahydropyranyl) | 0 | Me | H | — | — |
| 3-(2,2-dimethyltetrahydropyranyl) | 0 | Me | H | — | — |
| 3-(4,4-dimethyltetrahydropyranyl) | 0 | Me | H | — | — |
| 3-(2,4-dimethyltetrahydropyranyl) | 0 | Me | H | — | — |
| 3-(tetrahydrothienyl) | 0 | Me | H | — | — |
| 3-(tetrahydrothienyl) | 1 | Me | H | cyclopentyl | H |
| 3-(tetrahydrothienyl) | 2 | Me | H | cyclobutyl | H |
| 3-(4,5-dihydrothienyl) | 1 | Me | H | cyclopropyl | H |
| 3-(2,2,4,4-tetramethyltetrahydrothienyl) | 0 | Me | H | — | — |
| 3-(2,2,4-trimethyltetrahydrothienyl) | 0 | Me | H | — | — |
| 3-(2,4-dimethyltetrahydrothienyl) | 0 | Me | H | — | — |
| 3-(2,2-dimethyltetrahydrothienyl) | 0 | Me | H | — | — |
| 3-furyl | 1 | Me | H | H | H |
| 3-thienyl | 1 | Me | H | H | H |
| 3-(2,4,4-trimethyltetrahydrothienyl) | 0 | Me | H | — | — |
| 3-(2,2,4,4-tetramethyl-1,1-dioxo-tetrahydrothienyl) | 0 | Me | H | — | — |
| 3-(2,2,4,4-tetramethyl-1-oxo-tetrahydrothienyl) | 0 | Me | H | — | — |
| 3-(2,2,4-trimethyl-1,1-dioxo-tetrahydrothienyl) | 1 | Me | H | cyclopentyl | H |
| 3-(2,4-dimethyl-1,1-dioxo-tetrahydrothienyl) | 0 | Me | H | — | — |
| 3-(2,2-dimethyl-1,1-dioxo-tetrahydrothienyl) | 0 | Me | H | — | — |
| 3-(4,4-dimethyl-1,1-dioxo-tetrahydrothienyl) | 0 | Me | H | — | — |
| 3-(2,2,4-trimethyl-1-oxo-tetrahydrothienyl) | 0 | Me | H | — | — |
| 5-methylfuryl | 1 | Me | H | H | H |

-continued

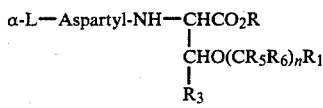

| R₁ | n | R | R₃ | R₅ | R₆ |
|---|---|---|---|---|---|
| 5-methylthienyl | 1 | Me- | H | H | H |

EXAMPLE 27

A cherry flavored beverage is prepared by mixing 1.48 gms. of an unsweetened instant beverage base mix with 438 gms. of water and 0.025 weight percent of L-aspartyl-S-(1-methylcyclopentyl)-L-cysteine methyl ester. The base contains a malic acid and monocalcium phosphate buffer, flavorants and colorants.

EXAMPLE 28

A vanilla flavored pudding is prepared by mixing 474 gms. of milk, 21.7 gms. of an unsweetened pudding base mix and 0.036 weight percent of L-aspartyl-S-(1-methyl-cyclohexyl)-L-cysteine methyl ester. The base contains Na₂HPO₄, tapioca starch emulsifiers, salt, flavorants and colorants.

Representative compounds of this invention were tested for sweetness with the results being given in Table 1.

TABLE 1

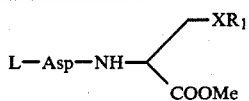

| XR₁ | Concentration of Compound (%) | Sucrose Equivalent (%) | Sweetness ratio (Compound:Sucrose) |
|---|---|---|---|
| O—t-butyl[a] | .05 | 6 | 120 |
| O—1-methyl-cyclopentyl | .005 | 2.5 | 500 |
| | .01 | 5 | 500 |
| | .025 | 10 | 400 |
| O—1-methyl-cyclohexyl | .005 | 2 | 400 |
| | .01 | 4.5 | 450 |
| | .025 | 8.5 | 340 |
| O—1-methyl-cyclobutyl | .01 | 2 | 200 |
| | .05 | 8 | 160 |
| O—Cis-1,2-dimethylcyclohexyl | .005 | 2 | 400 |
| | .010 | 4 | 400 |
| | .020 | 7 | 350 |
| O—trans-1,2-dimethylcyclohexyl | .005 | 1.5 | 300 |
| | .010 | 3 | 300 |
| | .020 | 5 | 250 |
| O—1-ethyl-cyclopentyl | .005 | 2 | 400 |
| | .01 | 4 | 400 |
| | .02 | 6 | 300 |
| O—1-bornyl | .005 | 1 | 200 |
| | .01 | 2.5 | 250 |
| | .025 | 4.5 | 180 |
| O—1-methyl-cyclo-3-hexenyl | .005 | 2 | 400 |
| | .01 | 2.5 | 250 |
| | .025 | 4 | 160 |
| O—2-(4-methyl-cyclohexyl)-isopropyl | .025 | 6 | 240 |
| | .05 | 11 | 220 |
| O—1-methyl-cycloheptyl | .01 | 2 | 200 |
| | .05 | 6 | 120 |
| O—[1,1-dimethyl-(4-methylcyclo-hex-3-enyl)-methyl] | .01 | 2.2 | 220 |
| | .025 | 5.2 | 208 |
| O—2-(4-norbornenyl)ethyl | .05 | 5.8 | 117 |
| O—2-nor- | .04 | 4.2 | 105 |

TABLE 1-continued

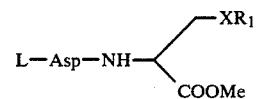

| XR₁ | Concentration of Compound (%) | Sucrose Equivalent (%) | Sweetness ratio (Compound:Sucrose) |
|---|---|---|---|
| bornenylethyl | | | |
| O—2,2,5,5-tetra-methylcyclopentyl | .0225 | 3 | 1200 |
| | .005 | 5 | 1000 |
| | .01 | 8 | 800 |
| O—cyclopentyl | .005 | 1.5 | 300 |
| | .01 | 2.3 | 230 |
| | .025 | 4.5 | 180 |
| O—cyclohexyl | .01 | 1.2 | 120 |
| | .025 | 3.2 | 128 |
| O—2-cis-cyclo-hexyl | .005 | 1.8 | 360 |
| | .01 | 3.2 | 320 |
| | .025 | 6 | 240 |
| O—2,2-dimethyl-cyclopentyl | .005 | 3 | 600 |
| | .01 | 5.3 | 530 |
| | .025 | 9 | 360 |
| O—trans-2-methylcyclopentyl | .01 | 3 | 300 |
| | .025 | 5.3 | 212 |
| S—1-methyl-cyclopentyl | .0025 | 5 | 2000 |
| | .005 | 6 | 1600 |

[a]previously known compound

In comparison with sweetness values observed with present new compounds, the corresponding alkyl ethers of L-aspartyl-L-serine methyl esters demonstrate a lower order of sweetness. Table 2 summarizes the sweetness values for representative alkyl ethers, as reported in the prior art.

TABLE 2

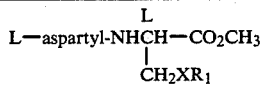

| R₁ | X | Sucrose Equivalent |
|---|---|---|
| tert. C₄H₉ | O | 140[a] |
| tert. C₅H₁₁ | O | 230[b] |
| methyl | S | 1[a] |
| ethyl | S | 40[a] |
| propyl | S | 130[a] |
| isopropyl | S | 170[a] |
| t-butyl | S | 900[a] |
| methyl | CH₂S | 80[a] |

[a]Van der Heijden, Brusse and Peer, Chemical Senses and Flavour, 4, 141-152 (1979).
[b]U.S. Pat. No. 3,798,204.

What is claimed is:

1. A composition comprising an edible composition and sweetening effective amount of a compound having the formula:

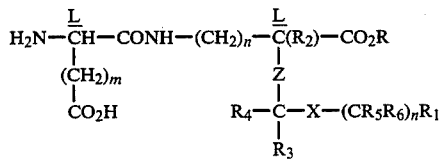

wherein
R is alkyl containing 1-3 carbon atoms;
when X=S
R₁ is cycloalkyl, cycloalkenyl, lower alkyl-substituted cycloalkyl or cycloalkenyl, bicycloalkyl, bicycloalkenyl, tricycloalkyl, aryl, alkylaryl, cyclic ether, cyclic thioether, cyclic sulfoxide or cyclic sulfone, containing up to 10 ring carbon atoms and up to a total of 12 carbon atoms;

when X=O

R$_1$ is cyclic ether or cyclic thioether containing up to 10 ring carbon atoms and up to a total of 12 carbon atoms;

R$_2$, R$_3$, R$_4$ and R$_6$ are each H or lower alkyl;

R$_5$ is H, lower alkyl or cycloalkyl containing up to 3-5 ring carbon atoms;

each n=0, 1 or 2;

m=0 or 1;

Z is an alkylene chain containing 0-2 carbon atoms in the principal chain and up to a total of 6 carbon atoms;

and food acceptable salts.

2. The composition of claim 1 which further comprises a food acceptable carrier.

3. The composition of claim 1 wherein the edible composition is a beverage.

4. The composition of claim 1 wherein the edible composition is a gelatin dessert.

5. The composition of 1 wherein the edible composition is a milk pudding.

6. The composition of claim 1 which further comprises an additional sweetener.

7. The composition of claim 6 wherein the additional sweetener is sucrose, fructose, corn syrup solids, dextrose, xylitol, sorbitol, mannitol, acetosulfam, thaumatin, invert sugar, saccharin, thiophenesaccharin, meta-aminobenzoic acid, meta-hydroxybenzoic acid, cyclamate, chlorosucrose, dihydrochalcone, hydrogenated glucose syrup, aspartame or other dipeptides, glycrrhizin or stevioside, or mixtures thereof.

8. The composition of claim 1 wherein the compound is α-L-aspartyl-S-(1-methylcyclopentyl)-L-cysteine methyl ester.

9. The composition of claim 1 wherein the compound is α-L-aspartyl-S-(1-ethylcyclopentyl)-L-cyclopentyl cysteine methyl ester.

10. The composition of claim 1 wherein the compound is α-L-aspartyl-S-(2,2,5,5-tetramethylcyclopentyl)-L-cysteine methyl ester.

11. The composition of claim 1 wherein the compound is α-L-aspartyl-S-(cyclopentyl)-L-cysteine methyl ester.

12. A composition comprising an edible commposition and a sweetening effective amount of a compound having the formula:

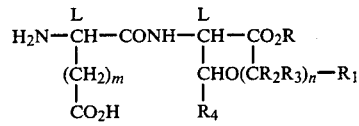

wherein R is alkyl containing 1-3 carbon atoms

R$_1$ is cyclic ether or cyclic thio-ether containing up to 10 ring carbon atoms and up to 12 carbon atoms;

R$_2$ and R$_4$ are each H alkyl containing 1-3 carbon atoms;

R$_3$ is H, alkyl containing 1-6 carbon atoms or cycloalkyl containing 3-5 ring carbon atoms;

n=0, 1 or 2; and m=0 or 1;

and food acceptable salts thereof.

13. The composition of claim 12 which further comprises a food acceptable carrier.

14. The composition of claim 12 wherein the edible composition is a beverage.

15. The composition of claim 12 wherein the edible composition is a gelatin dessert.

16. The composition of claim 12 wherein the edible composition is a milk pudding.

17. The composition of claim 12 which further comprises an additional sweetener.

18. The composition of claim 17 wherein the additional sweetener is sucrose, frustose, corn syrup solids, dextrose, xylitol, sorbitol, mannitol, acetosulfam, thaumatin, invert sugar, saccharin, thiophenesaccharin, meta-aminobenzoic acid, meta-hydroxybenzoic acid, cyclamate, chlorosucrose, dihydrochalcone, hydrogenated glucose syrup, aspartame or other dipeptides, glycrrhizin or stevioside, or mixtures thereof.

19. The composition of claim 12 where R$_1$ in the compound is tetrahydrofuryl or tetrahydrothienyl.

20. The composition of claim 12 wherein the compound is α-L-aspartyl-[O-(3-tetrahydrothienyl)]-L-serine methyl ester.

21. The composition of claim 12 wherein the compound is α-L-aspartyl-[O-3-(2,2,4,4-tetramethyltetrahydrothienyl)]-L-serine methyl ester.

22. The composition of claim 12 wherein the compound is α-L-aspartyl[O-3-(2,2,4-trimethyltetrahydrothienyl)]-L-serine methyl ester.

23. The composition of claim 12 wherein the compound is α-L-aspartyl[3-(2,4-diemethyltetrahydrothienyl)]-L-serine methyl ester.

24. The composition of claim 12 wherein the compound is α-L-aspartyl[3-(2,2-dimethyltetrahydrothienyl)]-L-serine methyl ester.

25. The composition of claim 12 wherein the compound is α-L-aspartyl[3-(2,4,4-trimethyltetrahydrothienyl)]-L-serine methyl ester.

* * * * *